United States Patent
Higeta et al.

(10) Patent No.: US 9,244,194 B2
(45) Date of Patent: Jan. 26, 2016

(54) AZO COMPOUND AND SALT THEREOF, AND DYE-BASED POLARIZING FILM AND POLARIZING PLATE CONTAINING THE SAME

(75) Inventors: Takahiro Higeta, Kita-ku (JP); Takuto Nishiguchi, Kita-ku (JP)

(73) Assignees: Nippon Kayaku Kabushiki Kaisha, Tokyo (JP); Polatechno Co., Ltd., Niigata (JP)

( * ) Notice: Subject to any disclaimer, the term of this patent is extended or adjusted under 35 U.S.C. 154(b) by 173 days.

(21) Appl. No.: 13/983,791

(22) PCT Filed: Feb. 6, 2012

(86) PCT No.: PCT/JP2012/000784
§ 371 (c)(1),
(2), (4) Date: Aug. 6, 2013

(87) PCT Pub. No.: WO2012/108173
PCT Pub. Date: Aug. 16, 2012

(65) Prior Publication Data
US 2013/0314786 A1 Nov. 28, 2013

(30) Foreign Application Priority Data
Feb. 7, 2011 (JP) ................. 2011-023748

(51) Int. Cl.
G02B 1/08 (2006.01)
G02B 1/04 (2006.01)
G02B 5/30 (2006.01)
C09B 31/30 (2006.01)
C09B 67/22 (2006.01)
C09B 49/04 (2006.01)
G02F 1/1335 (2006.01)

(52) U.S. Cl.
CPC . *G02B 1/04* (2013.01); *C09B 31/30* (2013.01); *C09B 49/04* (2013.01); *C09B 67/0046* (2013.01); *C09B 67/0055* (2013.01); *G02B 1/08* (2013.01); *G02B 5/305* (2013.01); *B32B 2457/202* (2013.01); *G02F 1/133533* (2013.01); *Y10T 428/1041* (2015.01)

(58) Field of Classification Search
CPC .... C09B 31/30; C09B 49/04; C09B 67/0046; C09B 31/0055; G02B 1/04; G02B 1/08; G02B 5/305; G02F 1/133533; Y10T 428/1041; B32B 2457/202
USPC ............... 428/1.31; 349/97; 359/487.02
See application file for complete search history.

(56) References Cited

U.S. PATENT DOCUMENTS 3,005,814 A 10/1961 Schweizer et al.
6,399,752 B1 6/2002 Ohta et al.

2003/0098447 A1* 5/2003 Ashida et al. ................. 252/585
2010/0257678 A1 10/2010 Sadamitsu et al.
2011/0075076 A1* 3/2011 Nishiguchi et al. ............ 349/96
2013/0302538 A1 11/2013 Higeta et al.

FOREIGN PATENT DOCUMENTS

| JP | 2622748 B2 | 6/1997 |
| JP | 2002-220544 A | 8/2002 |
| JP | 2002-275381 A | 9/2002 |
| JP | 2002-296417 A | 10/2002 |
| JP | 2003-64276 A | 3/2003 |
| JP | 2003-313451 A | 11/2003 |
| JP | 2003-327858 A | 11/2003 |
| JP | 2004-51645 A | 2/2004 |
| JP | 2005-255846 A | 9/2005 |
| JP | 2009-115866 A | 5/2009 |

(Continued)

OTHER PUBLICATIONS

International Search Report and Written Opinion mailed May 1, 2012 in co-pending PCT application No. PCT/JP2012/000775.

(Continued)

*Primary Examiner* — Sophie Hon
(74) *Attorney, Agent, or Firm* — Nields, Lemack & Frame, LLC

(57) ABSTRACT

The present invention relates to an azo compound represented by the following formula (1) [wherein, A represents a naphthyl group having a substituent, $R_1$ to $R_6$ each independently represent a hydrogen atom, an alkyl group having a carbon atom number of 1 to 5, an alkoxy group having a carbon atom number of 1 to 5, a sulfo group, or an alkoxy group having a sulfo group and a carbon atom number of 1 to 5, and X represents a benzoylamino group having a substituent, a phenylamine group having a substituent, a phenylazo group having a substituent, or a naphthotriazole group having a substituent] and a salt thereof. A neutral color polarizing plate and a color polarizing plate for a liquid crystal projector being excellent in polarization performance and durability and having less color leakage in a visible light region can be provided.

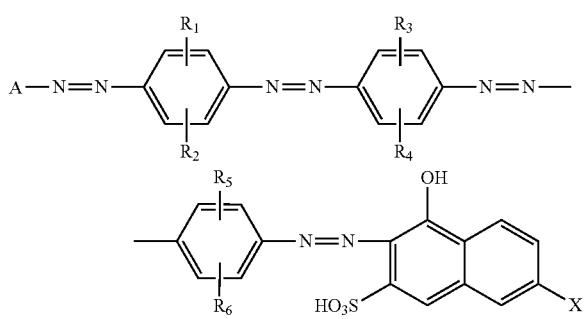

17 Claims, No Drawings

(56) References Cited

FOREIGN PATENT DOCUMENTS

| WO | 2007/148757 A1 | 12/2007 | |
|---|---|---|---|
| WO | WO 2009142193 A1 * | 11/2009 | ............... G02B 5/30 |
| WO | 2012/108169 A1 | 8/2012 | |

OTHER PUBLICATIONS

International Preliminary Report on Patentability mailed Aug. 22, 2013 in co-pending PCT application No. PCT/JP2012/000775.
International Search Report and Written Opinion mailed May 1, 2012 in corresponding PCT application No. PCT/JP2012/000784.
International Preliminary Report on Patentability mailed Aug. 22, 2013 in corresponding PCT application No. PCT/JP2012/000784.
Taiwanese communication, with English translation, dated Jan. 13, 2015 in co-pending Taiwanese patent application No. 101103856.
Office Action mailed Apr. 9, 2015 in co-pending U.S. Appl. No. 13/980,184.
Taiwanese communication, with English translation, dated Jan. 13, 2015 in corresponding Taiwanese patent application No. 101103860.
Notice of Allowance mailed Sep. 25, 2015 in co-pending U.S. Appl. No. 13/980,184.
Office action mailed Sep. 9, 2015 in co-pending U.S. Appl. No. 14/813,163.
Office action mailed Sep. 9, 2015 in co-pending U.S. Appl. No. 14/813,166.

* cited by examiner

AZO COMPOUND AND SALT THEREOF, AND DYE-BASED POLARIZING FILM AND POLARIZING PLATE CONTAINING THE SAME

TECHNICAL FIELD

The present invention relates to a novel azo compound and a salt thereof, a dye-based polarizing film containing them, and a polarizing plate.

BACKGROUND ART

The polarizing plate having light transmission/shielding function and also a liquid crystal having light switching function are fundamental components of display devices such as liquid crystal displays (Liquid Crystal Display: LCD). The application field of this LCD has been also extended from small instruments such as initial electronic calculators and clocks to laptop personal computers, word processors, liquid crystal projectors, liquid crystal televisions, car navigation systems and indoor-outdoor measurement instruments, and the like. In addition, it can be also applied to a lens having polarization function, and has been applied to sunglasses with improved visibility and also, in recent years, polarized glasses for 3D televisions, and the like. As above, the application of the polarizing plate is widely broadened and it is used under broad conditions from low temperature to high temperature, from low humidity to high humidity, and from low light amount to high light amount, so a polarizing plate having high polarization performance and excellent durability is required.

At present, the polarizing film is manufactured by dyeing, with iodine or a dichroic dye as a dichroic coloring matter, a polarizing raw film such as a film formed by stretching and orienting polyvinyl alcohol or a derivative thereof or a polyene-based film formed by producing a polyene by dehydrochlorination of a polyvinyl chloride film or by dehydration of a polyvinyl alcohol-based film and then orienting the polyene, or manufactured by allowing iodine or a dichroic dye as a dichroic coloring matter to be contained in the polarizing raw base. Among them, the iodine-based polarizing film using iodine as a dichroic coloring matter has excellent polarization performance but is vulnerable to water and heat, and thus it has a problem with its durability when used in the state of high temperature and high humidity for a long period of time. Some solution methods have been considered, such as treatment with formalin or an aqueous solution containing boric acid and use of a polymer film having a low water-vapor transmission ratio as a protective film, in order to improve durability, but their effects are not sufficient. On the other hand, the dye-based polarizing film using a dichroic dye as a dichroic coloring matter is excellent in moisture fastness and heat fastness as compared with the iodine-based polarizing film but generally has insufficient polarization performance.

In a neutral-color polarizing film formed by adsorption of a few kinds of dichroic dyes into a polymer film and by orientation, if light-leakage (color-leakage) of a certain wavelength in a wavelength region of a visible light region occurs in the state where two polarizing films are superposes so that their orientation direction are orthogonal (in the orthogonal position), the hue of a liquid crystal display could change in a dark state when the polarizing film is provided on a liquid crystal panel. In order to prevent discoloration of a liquid crystal display due to color leakage in a certain wavelength in the dark state when a liquid crystal display is provided with a polarizing film, the transmittance ratio in the orthogonal position (orthogonal transmittance ratio) in the wavelength region of the visible light region must be uniformly reduced in a neutral color polarizing film formed by adsorption of a dichroic dye into a plural kinds of polymer films and by orientation.

In the case of a color liquid crystal projection-type display, i.e., a color liquid crystal projector, a polarizing plate is used in its liquid crystal image formation part. Previously, an iodine-based polarizing plate having good polarization performance and exhibiting neutral gray was used. However, the iodine-based polarizing plate has a problem of insufficiency in light fastness, heat fastness and wet-heat fastness because iodine is used as a dichroic coloring matter as described above. In order to solve this problem, a neutral gray polarizing plate with a dye-based dichroic coloring matter being a polarizer has been increasingly used. For this neutral-gray polarizing plate, coloring matters of three primary colors are usually used in combination in order to averagely improve the transmittance in all visible light wavelength regions and polarization performance. For this reason, a neutral gray polarizing plate using a dichroic dye as a dichroic coloring matter does not have sufficient light transmittance, so there is a problem that the light source intensity must be higher in order to meet market needs of a brighter projection image in a color liquid crystal projector. In order to solve this problem, three color dye-based polarizing plates corresponding to three primary colors, i.e., for blue channel, green channel and red channel, have been used instead of the neutral gray polarizing plate.

However, reduction in brightness cannot be avoided due to considerable absorption of light by a polarizing plate, enlargement of an image having a small area of 0.5-3 inches to a few dozen-hundred inches, and so on, and therefore as its light source, one having higher luminance is used. Additionally, further improvement of brightness of a liquid crystal projector is firmly required, and as a result, intensity of a light source used has been increasingly enhanced, which also involves increase in light and heat on a polarizing plate.

The dye used for manufacturing the above-described dye-based polarizing film includes, for example, water-soluble azo compounds described in Patent Literature 1 to Patent Literature 7, and the like.

However, conventional polarizing plates containing the above water-soluble dye have yet to sufficiently satisfy market needs from the viewpoint of polarization properties, absorption in wavelength region, hue and the like. In addition, for the three color dye-based polarizing plates for blue channel, green channel and red channel corresponding to three primary colors for a color liquid crystal projector, there is no polarizing plate having brightness and polarization performance and being good in all of durability under high temperature and high humidity conditions and also fastness to light exposure for a long period of time, so improvement of conventional polarizing plates is desired.

Patent Literature 1: Japanese Patent No. 2622748 A
Patent Literature 2: Japanese Patent Laid-Open No, 2001-33627 A
Patent Literature 3: Japanese Patent Laid-Open No. 2004-51645 A
Patent Literature 4: WO2005/075572 A
Patent Literature 5: WO2007/148757 A
Patent Literature 6: Japanese Patent Laid-Open No. 2003-327858 A
Patent Literature 7: Japanese Patent Laid-Open No. 2005-255846 A
Patent Literature 8: Japanese Patent Laid-Open No. 2004-075719 A
Non-Patent Literature 1: Dye Chemistry; written by Yutaka Hosoda

DISCLOSURE OF THE INVENTION

Problems to be Solved by the Invention

One of the objects of the present invention is to provide a high-performance polarizing plate having excellent polarization performance and moisture, heat and light fastnesses. In addition, another object of the present invention is to provide a neutral-color polarizing plate formed by adsorption of two or more kinds of dichroic dyes into a polymer film and by orientation, where the polarizing plate is a high-performance polarizing plate causing no color-leakage in the orthogonal position in the visible light wavelength region and having excellent polarization performance and moisture, heat and light fastnesses.

A further object is to provide a high-performance polarizing plate corresponding to three primary colors for a color liquid crystal projector and being good in all of brightness, polarization performance, durability and light fastness.

Means of Solving the Problems

The present inventors have intensively studied to achieve the objects and found that a polarizing film and a polarizing plate containing a certain azo compound and a salt thereof have excellent polarization performance and moisture, heat and light fastnesses, and thus the present invention has been completed.

That is, the present invention relates to the invention described in (1) to (21) below.

(1)
An azo compound represented by the following formula (1):

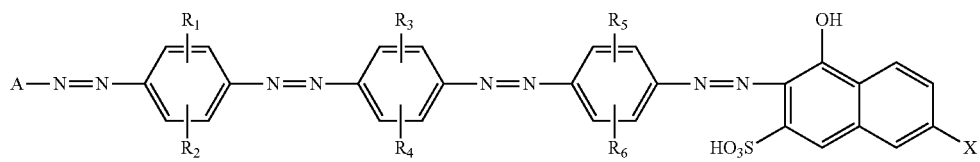

wherein, A represents a naphthyl group having a substituent; $R_1$ to $R_6$ each independently represent a hydrogen atom, an alkyl group having a carbon atom number of 1 to 5, an alkoxy group having a carbon atom number of 1 to 5, a sulfo group or an alkoxy group having a sulfo group and a carbon atom number of 1 to 5; and X represents a benzoylamino group having a substituent, a phenylamino group having a substituent, a phenylazo group having a substituent, or a naphthotriazole group having a substituent and/or a salt thereof.

(2)
The azo compound and/or a salt thereof according to the above-described (1), wherein X is a benzoylamino group having a substituent, a phenylamino group having a substituent, a phenylazo group having a substituent, or a naphthotriazole group having a substituent, and these substituents are groups selected from the group consisting of a hydrogen atom, an alkyl group having a carbon atom number of 1 to 5, an alkoxy group having a carbon atom number of 1 to 5, a hydroxy group, a carboxy group, a sulfo group, an amino group or a substituted amino group.

(3)
The azo compound and/or a salt thereof according to the above-described (1), wherein X is a phenylamino group represented by the following formula (2):

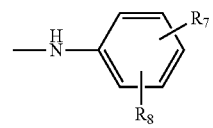

in the formula (2), $R_7$ and $R_8$ each independently represent a hydrogen atom, a methyl group, a methoxy group, a sulfo group, an amino group or a substituted amino group.

(4)
The azo compound and/or a salt thereof according to the above-described (1), wherein X is a benzoylamino group represented by the following formula (3):

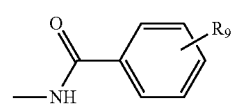

in the formula (3), $R_9$ represents a hydrogen atom, a hydroxy group, an amino group or a substituted amino group.

(5)
The azo compound and/or a salt thereof according to the above-described (1), wherein X is a naphthotriazole group represented by the following formula (4):

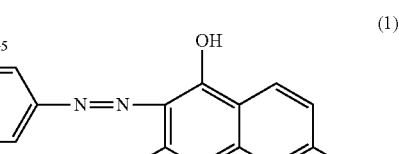

in the formula (4), m represents 1 or 2.

(6)
The azo compound and/or a salt thereof according to the above-described (1), wherein X is a phenylazo group represented by the following formula (5):

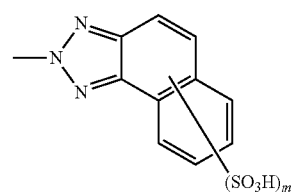

in the formula (5), $R_{10}$ to $R_{12}$ each independently represent a hydrogen atom, a hydroxy group, an alkyl group having a carbon atom number of 1 to 5, an alkoxy group having a carbon atom number of 1 to 5, an amino group or a substituted amino group.

(7)
The azo compound and/or a salt thereof according to any one of the above-described (1) to (6), wherein A is a naphthyl group having at least one substituent and at least one of the substituents is a sulfo group.

(8)
The azo compound and/or a salt thereof according to any one of the above-described (1) to (6), wherein A is a naphthyl group represented by the following formula (6):

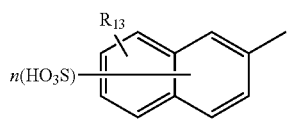

in the formula (6), $R_{13}$ represents a hydrogen atom, a hydroxy group, or an alkoxy group having a sulfo group and a carbon atom number of 1 to 5, and n represents 1 to 3.

(9)
The azo compound or/and a salt thereof according to any one of the above-described (1) to (8), wherein $R_1$ to $R_6$ are each independently a hydrogen atom, a methyl group, a methoxy group, or an alkoxy group having a sulfo group and a carbon atom number of 1 to 5.

(10)
The azo compound or/and a salt thereof according to any one of the above-described (1) to (9), which is represented by the following formula (7):

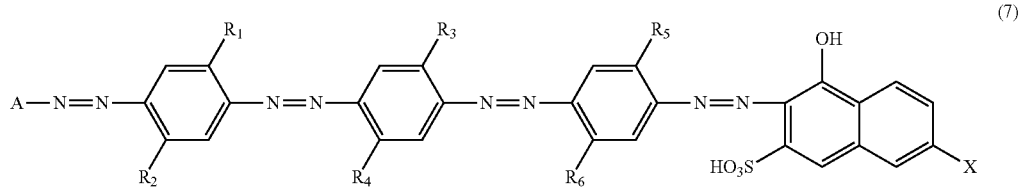

in the following formula (7), A, $R_1$ to $R_6$ and X have the same meanings as A, $R_1$ to $R_6$ and X in the formula (1).

(11)
The azo compound and/or a salt thereof according to any one of the above-described (1) to (10), wherein A is a naphthyl group substituted with 2 or 3 sulfo groups or a naphthyl group substituted with a 3-sulfopropoxy group and a sulfo group; $R_1$, $R_3$ and $R_5$ are each independently a hydrogen atom, a methyl group, a methoxy group or a 3-sulfopropoxy group; $R_2$, $R_4$ and $R_6$ are methyl groups; and X is any one group selected from the group consisting of an unsubstituted phenylamino group, a phenylamino group substituted with a methoxy group, a benzoylamino group substituted with an amino group, and a naphthotriazole group substituted with 2 sulfo groups.

(12)
A dye-based polarizing film containing the azo compound and/or a salt thereof according to any one of the above-described (1) to (11) in a raw film for a polarizing film.

(13)
A dye-based polarizing film containing the azo compound and/or a salt thereof according to any one of the above-described (1) to (11) and one or more kinds of dichroic organic dyes other than it in a raw film for a polarizing film.

(14)
A dye-based polarizing film containing two or more kinds of the azo compound and/or a salt thereof according to any one of the above-described (1) to (11) and one or more kinds of dichroic organic dyes other than it in a raw film for a polarizing film.

(15)
A color dye-based polarizing film containing at least one kind of the azo compound and/or a salt thereof according to any one of the above-described (1) to (11) in a raw film for a polarizing film.

(16)
The dye-based polarizing film according to any one of the above-described (12) to (15), wherein the raw film for a polarizing film is a film comprising a polyvinyl alcohol resin, a vinyl alcohol copolymer resin or a modified form of a polyvinyl alcohol resin.

(17)
The dye-based polarizing film according to the above-described (16), wherein the raw film for a polarizing film is a polyvinyl alcohol resin film.

(18)
A dye-based polarizing plate with a transparent protective film attached to at least one surface of the dye-based polarizing film according to any one of the above-described (12) to (17).

(19)
Use of the dye-based polarizing film according to any one of the above-described (12) to (17) or the dye-based polarizing plate according to the above-described (18) for manufacturing a liquid crystal display.

(20)
Use of the dye-based polarizing film according to any one of the above-described (12) to (17) or the dye-based polarizing plate according to the above-described (18) for manufacturing a liquid crystal projector.

(21)
A liquid crystal display comprising the dye-based polarizing plate according to the above-described (18).

Effect of the Invention

The azo compound or a salt thereof of the present invention is useful as a dichroic dye for a polarizing film and has high water-solubility. And polarizing films containing these compounds have high optical performance (for example, high polarization ratio and high contrast) comparable to the polarizing film using iodine and are excellent also in durability. For that reason, they are suitable for various liquid crystal display bodies and liquid crystal projectors, in-vehicle application requiring high optical performance and durability, and display application in industrial instruments used in various environments.

BEST MODE FOR CARRYING OUT THE INVENTION

The azo compound of the present invention is represented by the above-described formula (1).

In the above-described formula (1), A represents a naphthyl group having a substituent, $R_1$ to $R_6$ each independently represent, a hydrogen atom, an alkyl group having a carbon atom number of 1 to 5, an alkoxy group having a carbon atom number of 1 to 5, a sulfo group, or an alkoxy group having a sulfo group and a carbon atom number of 1 to 5, X represents an amino group having a substituent, a benzoylamino group having a substituent, a phenylamino group having a substituent, a phenylazo group having a substituent, or a naphthotriazole group having a substituent.

Hereinafter, the compound represented by the formula (1) will be explained. In explanation of substituent and the like, "lower" described in "lower alkyl", "lower alkoxy" and the like means that the carbon atom number is 1 to 5.

In addition, "substituent" described in "having a substituent" in the present description includes a hydrogen atom unless otherwise noted in particular, which is explained as a "substituent" for convenience. In this regard, when the number of substituents is described in terms "at least one substituent", "two or more substituents" or the like, the described number means the number of substituents other than a hydrogen atom. Meanwhile, the substituted amino group includes a lower alkylcarbonylamino group having a water-soluble substituent, such as a sulfo group, a carboxy group or the like.

A represents a naphthyl group having a substituent. The substituent in the naphthyl group represented by A does not include a hydrogen atom and includes a sulfo group, a hydroxy group, an amino group, a substituted amino group, a nitro group, a substituted amide group, or an alkoxy group having a sulfo group and a carbon atom number of 1 to 5, and it is preferably a sulfo group, a hydroxy group, or an alkoxy group having a sulfo group and a carbon atom number of 1 to 5. It is preferred that the substituent in the naphthyl group represented by A preferably is at least one sulfo group. When the naphthyl group represented by A has two or more substituents, it is preferred that one of the substituents is a sulfo group and the other substituent is at least one selected from the group consisting of a sulfo group, a hydroxy group, and an alkoxy group having a sulfo group and a carbon atom number of 1 to 5. The alkoxy group having a sulfo group and a carbon atom number of 1 to 5 is preferably a straight-chain alkoxy group having a sulfo group and a carbon atom number of 1 to 5, more preferably a straight-chain alkoxy group having a sulfo group at a terminal of the alkoxy group and a carbon atom number of 1 to 5, and further preferably a 3-sulfopropoxy group or a 4-sulfobutoxy group.

The naphthyl group represented by A is preferably a naphthyl group substituted with 2 or 3 sulfo groups or a naphthyl group substituted with at least one selected from the group consisting of a hydroxy group, a 3-sulfopropoxy group and a 4-sulfobutoxy group and substituted with 1 or 2 sulfo groups; and more preferably a naphthyl group substituted with 2 or 3 sulfo groups or a naphthyl group substituted with a 3-sulfopropoxy group and a sulfo group. In addition, in some cases, a disulfonaphthyl group or a trisulfonaphthyl group is further preferable and a trisulfonaphthyl group is most preferable. The preferable substitution positions of these substituents on the naphthalene ring are the 1- and 3-positions in the case of 2 substituents and the 1-, 3- and 6-positions in the case of 3 substituents.

The substitution position of the azo group in said naphthyl group is preferably the 2-position.

In the above formula (1), the group represented by A is preferably a group represented by the following formula (6).

Formula (6)

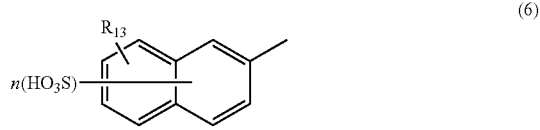

In the formula, $R_{13}$ represents a hydrogen atom, a hydroxy group, or an alkoxy group having a sulfo group and a carbon atom number of 1 to 5, and n represents an integer number of 1 to 3.

$R_{13}$ in the above-described formula (6) is preferably a hydrogen atom, a hydroxy group, a 3-sulfopropoxy group or a 4-sulfobutoxy group, and a hydrogen atom or a 3-sulfopropoxy group is preferable. In the above-described formula (6), when $R_{13}$ is an alkoxy group having a sulfo group and a carbon atom number of 1 to 5, and preferably a sulfopropoxy group, n is preferably 1. On the other hand, when $R_{13}$ is a hydrogen atom, n is preferably 2 or 3 and more preferably 3.

The preferable substitution positions are the 1- and 3-positions and the 6-position, when the azo group is at the 7-position.

In the above formula (1), X represents a benzoylamino group having a substituent, a phenylamino group having a substituent, a phenylazo group having a substituent, or a naphthotriazole group having a substituent.

When X is a benzoylamino group having a substituent, a phenylamino group having a substituent, or a phenylazo group having a substituent, its substituent is preferably a hydrogen atom, an alkyl group having a carbon atom number of 1 to 5, an alkoxy group having a carbon atom number of 1 to 5, a hydroxy group, a carboxy group, a sulfo group, an amino group or a substituted amino group.

When X is a phenylamino group having a substituent, its substituent is preferably a group selected from the group consisting of a hydrogen atom, a methyl group, a methoxy group, an amino group, a substituted amino group and a sulfo group. The number of substituents other than a hydrogen atom is usually 1 or 2 and preferably 1. The phenylamino group having a substituent is more preferably an unsubstituted phenylamino group or a phenylamino group having at least one group selected from the group consisting of a methyl group, a methoxy group, an amino group, a substituted amino group and a sulfo group as a substituent, and particularly preferably an unsubstituted phenylamino group or a phenylamino group substituted with a methoxy group.

The substitution position when said phenylamino group has a substituent is not particularly limited, but it is preferred that at least one substituent is at the p-position relative to the amino group.

When X is a phenylamino group having a substituent, it is preferably a phenylamino group represented by the following formula (2).

Formula (2)

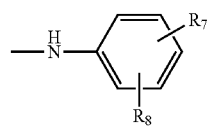

In the formula, $R_7$ and $R_8$ each independently represent a hydrogen atom, a methyl group, a methoxy group, a sulfo group, an amino group or a substituted amino group, and preferably a hydrogen atom, a methyl group, a methoxy group or an amino group. It is preferred that one of $R_7$ and $R_8$ is a hydrogen atom or a sulfo group and the other is a hydrogen atom, a methoxy group or an amino group, and it is further preferred that all of $R_7$ and $R_8$ are hydrogen atoms or that one of $R_7$ and $R_8$ is a hydrogen atom and the other is a methoxy group.

Specific examples of the phenylamino group having a substituent include, for example, a phenylamino group, a 4-methylphenylamino group, a 4-methoxyphenylamino group, a 4-aminophenylamino group, a 4-amino-2-sulfophenylamino group, a 4-amino-3-sulfophenylamino group, a 4-sulfomethylaminophenylamino group, a 4-(2-carboxyethylamino) phenylamino group, and the like. The preferable one can include a phenylamino group or a 4-methoxyphenylamino group.

When X is a benzoylamino group having a substituent, its substituent is preferably a hydrogen atom, an amino group, a substituted amino group or a hydroxy group, and particularly preferably a hydrogen atom or an amino group. The benzoylamino group having a substituent is preferably an unsubstituted benzoylamino group or a benzoylamino group having at least one group selected from the group consisting of an amino group, a substituted amino group and a hydroxy group as a substituent, and particularly preferably a benzoylamino group substituted with an amino group. The substitution position when said benzoylamino group has a substituent is not particularly limited, but preferably the p-position relative to the carbonyl group.

When X is a benzoylamino group having a substituent, it is preferably a benzoylamino group represented by the following formula (3).

Formula (3)

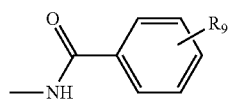

(3)

In the formula, $R_9$ represents a hydrogen atom, a hydroxy group, an amino group or a substituted amino group. Said substituted amino group includes, for example, a 3-carboxy-1-oxopropylamino group and a 2-carboxymethoxy-1-oxoethylamino group. $R_9$ in the formula (3) is preferably an amino group.

Specific examples of the benzoylamino group having a substituent, for example, a benzoylamino group, a 4-aminobenzoylamino group, a 4-hydroxybenzoylamino group, a 4-(3-carboxy-1-oxopropylamino)benzoylamino group, a 4-(2-carboxymethoxy-1-oxoethylamino)benzoylamino group and the like.

When X is a naphthotriazole group having a substituent, its substituent is preferably a sulfo group. The naphthotriazole group having a substituent is more preferably a naphthotriazole group substituted with 1 or 2 sulfo groups and further preferably a naphthotriazole group substituted with 2 sulfo groups.

When X is a naphthotriazole group having a substituent, it is preferably a 2H-naphtho[1,2-d]triazole-2-yl group represented by the following formula (4).

Formula (4)

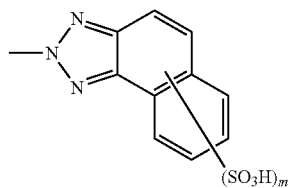

(4)

In the formula (4), m represents 1 or 2 and is preferably 2.

Specific examples of the naphthotriazole group having a substituent include, for example, a 6,8-disulfonaphthotriazole group, a 7,9-disulfonaphthotriazole group, a 7-sulfonaphthotriazole group, a 5-sulfo naphthotriazole group or the like.

Among them, a 6,8-disulfonaphthotriazole group is more preferable.

When X is a phenylazo group having a substituent, its substituent is preferably a hydroxy group, an amino group, a methyl group, a methoxy group or a carboxy group, and particularly preferably a hydroxy group.

When X is a phenylazo group having a substituent, it is preferably a phenylazo group represented by the following formula (5).

Formula (5)

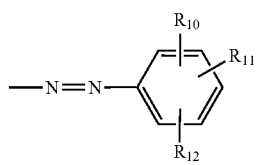

(5)

In the formula, $R_{10}$ to $R_{12}$ each independently represent a hydrogen atom, a hydroxy group, an alkyl group having a carbon atom number of 1 to 5 (preferably methyl group), an alkoxy group having a carbon atom number of 1 to 5 (preferably methoxy group), an amino group, or a substituted amino group (preferably carboxy lower alkylamino group). The combination of $R_{10}$ to $R_{12}$ is preferably a combination where any one thereof is a hydroxy group or an amino group, one of the rest is a hydrogen atom, a carboxy group or a methoxy group and the rest one is a hydrogen atom, and particularly preferably a combination where any one thereof is a hydroxy group and the rest two are hydrogen atoms.

Specific examples of the phenylazo group having a substituent includes, for example, a 2-methylphenylazo group, a 3-methylphenylazo group, a 2,5-dimethylphenylazo group, a 3-methoxyphenylazo group, a 2-methoxy-5-methylphenylazo group, a 2,5-dimethoxyphenylazo group, a 4-aminophenylazo group, a 4-hydroxyphenylazo group or a 4-(2-carboxyethylamino)phenylazo group, a 3-carboxy-4-hydroxyphenylazo group, a 4-hydroxy-3-methoxyphenylazo group and the like, and it is preferably a 4-aminophenylazo group, a 4-hydroxyphenylazo group, or a 4-(2-carboxyethylamino)phenylazo group, a 3-carboxy-4-hydroxyphenylazo group and a 4-hydroxy-3-methoxyphenylazo group.

X in the formula (1) is preferably a group represented by any of the above-described formulas (2) to (5) and it is more preferred that the groups represented by the above-described formulas (2) to (5) are the above-described preferable groups.

Preferable X in the formula (1) is any group selected from the group consisting of an unsubstituted phenylamino group, a methoxy-substituted phenylamino group, an amino-substituted benzoylamino group, a disulfo-substituted naphthotriazole group and a hydroxy-substituted phenylazo group.

More preferable X is, among the above, any group selected from the group consisting of an unsubstituted phenylamino group, a methoxy-substituted phenylamino group, an amino-substituted benzoylamino group and a disulfo-substituted naphthotriazole group, and particularly preferable X is, among the above, any group selected from the group consisting of an unsubstituted phenylamino group, a methoxy-substituted phenylamino group and amino-substituted benzoylamino group.

$R_1$ to $R_6$ in the above formula (1) each independently represent a hydrogen atom, an alkyl group having a carbon atom number of 1 to 5, an alkoxy group having a carbon atom number of 1 to 5, a sulfo group, or an alkoxy group having a sulfo group and a carbon atom number of 1 to 5, they are each preferably a hydrogen atom, a methyl group, an ethyl group, a methoxy group, an ethoxy group, a sulfo group, or an alkoxy group having a sulfo group and a carbon atom number of 1 to 5.

The alkoxy group having a sulfo group and a carbon atom number of 1 to 5 is preferably a straight-chain alkoxy group and the position of the sulfo group is preferably a terminal of the alkoxy group. Specifically, it is more preferably a 3-sulfopropoxy group or a 4-sulfobutoxy group.

$R_1$ to $R_6$ are, each independently, more preferably any group selected from the group consisting of a hydrogen atom, a methyl group, a methoxy group, a 3-sulfopropoxy group and a 4-sulfobutoxy group, and further preferably, each independently, any group selected from the group consisting of a hydrogen atom, a methyl group, a methoxy group and a 3-sulfopropoxy group.

In the formula (1) and the above case, one preferable aspect is that each phenylene group in the formula (1) has at least one group other than a hydrogen atom (for example, at least one of $R_1$ and $R_2$, of $R_3$ and $R_4$ and of $R_5$ and $R_6$ is a group other than hydrogen, respectively), and more preferably that each phenylene group has at least one methyl group. It is particularly preferred that $R_1$ to $R_6$ are each independently a hydrogen atom or a methyl group, each phenylene group has at least one methyl group and the total number of methyl groups is 3 to 6.

The substitution position for $R_1$ to $R_6$ on the phenylene group in the above formula (1) are preferably the 2-position only, the 3-position only, a combination of the 2-position and the 6-position, a combination of the 2-position and the 5-position and a combination of the 3-position and the 5-position, counting from the bond position of the azo group on the naphthyl group side, and particularly preferably the 2-position only, the 5-position only, and a combination of the 2-position and the 5-position. In this regard, "the 2-position only" or "the 3-position only" in the above means that only the 2-position or the 3-position has one substituent other than a hydrogen atom.

The azo compound represented by the above formula (1) or a salt thereof is preferably an azo compound represented by the following formula (7) or a salt thereof wherein the substitution position for $R_1$, $R_3$ and $R_5$ is the 2-position and the substitution position for $R_2$, $R_4$ and $R_6$ is the 5-position.

Formula (7)

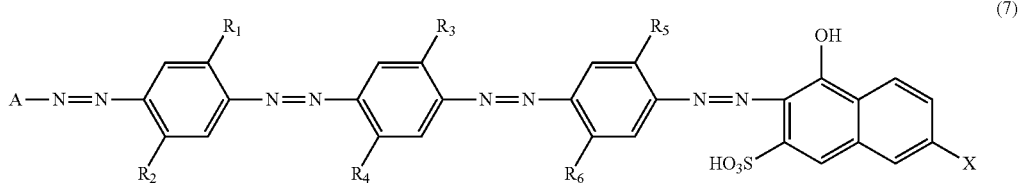

(7)

A, $R_1$ to $R_6$ and X in the formula (7) have the same meanings as A, $R_1$ to $R_6$ and X in the above formula (1).

In the azo compound represented by the above formula (1) or the above-described formula (7) or a salt thereof, one of the preferable aspects of $R_1$ to $R_6$ is that $R_1$, $R_3$ and $R_5$ are each independently any group selected from the group consisting of a hydrogen atom, a methyl group, a methoxy group, a 3-sulfopropoxy group and a 4-sulfobutoxy group and $R_2$, $R_4$ and $R_6$ are each independently any group selected from the group consisting of a methyl group and a methoxy group. In addition, one of the more preferable aspects is that $R_1$, $R_3$ and $R_5$ are each independently any group selected from the group consisting of a hydrogen atom, a methyl group, a methoxy group and a 3-sulfopropoxy group and $R_2$, $R_4$ and $R_6$ are methyl groups. Further, one of the preferable aspects is that $R_1$, $R_3$ and $R_5$ are each independently a hydrogen atom or a methyl group and $R_2$, $R_4$ and $R_6$ are methyl groups.

Preferable azo compounds represented by the above formula (1) or (7) or a salt thereof are as follows.

(i)
An azo compound represented by the above formula (1) or (7) or a salt thereof, wherein a naphthyl group represented by A has two or more substituents, one of its substituents is a sulfo group, the other substituent is a group selected from the group consisting of a sulfo group, a hydroxy group, and an alkoxy group having a sulfo group and a carbon atom number of 1 to 5, and $R_1$ to $R_6$ are each independently any group selected from the group consisting of a hydrogen atom, a methyl group, a methoxy group, a 3-sulfopropoxy group and a 4-sulfobutoxy group.

(ii)
The azo compound or a salt thereof according to the above-described (i), wherein A is (a) a naphthyl group substituted with 2 or 3 sulfo groups or (b) a naphthyl group substituted with at least one group selected from the group consisting of a hydroxy group, a 3-sulfopropoxy group and a 4-sulfobutoxy group and substituted with 1 or 2 sulfo groups.

(iii)
The azo compound or a salt thereof according to the above-described (i) or (ii), wherein X is any group selected from the group consisting of (a) an unsubstituted phenylamino group or (b) a phenylamino group having at least one group selected from the group consisting of a methyl group, a methoxy group, an amino group, a substituted amino group and a sulfo group as a substituent, (c) an unsubstituted benzoylamino group or a benzoylamino group having at least one group selected from the group consisting of an amino group, a substituted amino group and a hydroxy group as a substituent, (d) a sulfo-substituted naphthotriazole group, and (e) a phenylazo group having a hydroxy group, an amino group, a methyl group, a methoxy group or a carboxy group as a substituent.

(iv)
The azo compound or a salt thereof according to any one of the above-described (i) to (iii), wherein A is a naphthyl group represented by the above formula (6), $R_{13}$ in the formula (6) is a group selected from the group consisting of a hydrogen atom, a hydroxy group, and an alkoxy group having a sulfo group and a carbon atom number of 1 to 5, and preferably a hydrogen atom or a 3-sulfopropoxy group, and n is an integer number of 1 to 3.

(v)
The azo compound or a salt thereof according to any one of the above-described (i) to (iv), wherein $R_1$, $R_3$ and $R_5$ are each independently any group selected from the group consisting of a hydrogen atom, a methyl group, a methoxy group and a 3-sulfopropoxy group, and $R_2$, $R_4$ and $R_6$ are methyl groups.

(vi)
The azo compound or a salt thereof according to any one of the above-described (i) to (v), wherein X is any group selected from the group consisting of an unsubstituted phenylamino group, a phenylamino group substituted with a methoxy group, a benzoylamino group substituted with an amino group, a naphthotriazole group substituted with 2 sulfo groups, and a phenylazo group substituted with a hydroxy group.

(vii)
The azo compound or a salt thereof according to any one of the above-described (i) to (vi), wherein A is a trisulfonaphtyl group.

(viii)
The azo compound or a salt thereof according to any one of the above-described (i) to (vii), wherein $R_1$, $R_3$ and $R_5$ are each independently a hydrogen atom or a methyl group and $R_2$, $R_4$ and $R_6$ are methyl groups.

(ix)
The azo compound or a salt thereof according to any one of the above-described (i) to (viii), wherein X is any group selected from the group consisting of an unsubstituted phenylamino group, a phenylamino group substituted with a methoxy group, a benzoylamino group substituted with an amino group, and a naphthotriazole group substituted with 2 sulfo groups, and preferably any group selected from the group consisting of an unsubstituted phenylamino group, a phenylamino group substituted with a methoxy group, and a benzoylamino group substituted with an amino group.

(x)
An azo compound or a salt thereof of the formula (1) or (7) or the azo compound or a salt thereof according to any one of the above-described (i) to (vi), wherein the number of sulfo groups in the formula (1) or (7) is at least four in total.

Next, specific examples of the azo compounds represented by the above-described formula (1) used in the present invention are listed in the following Table A to Table G. In this regard, the sulfo group, the carboxy group and the hydroxy group in the formula are shown in free acid form.

TABLE A

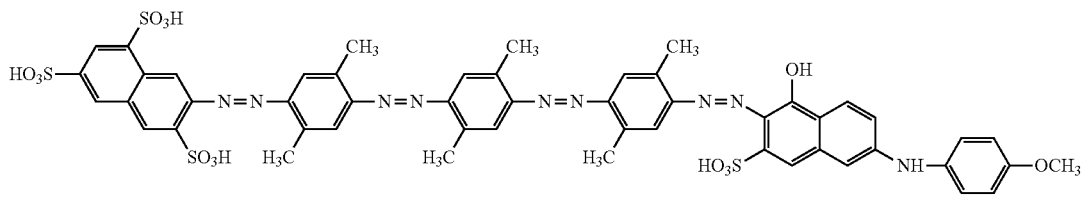

(8)

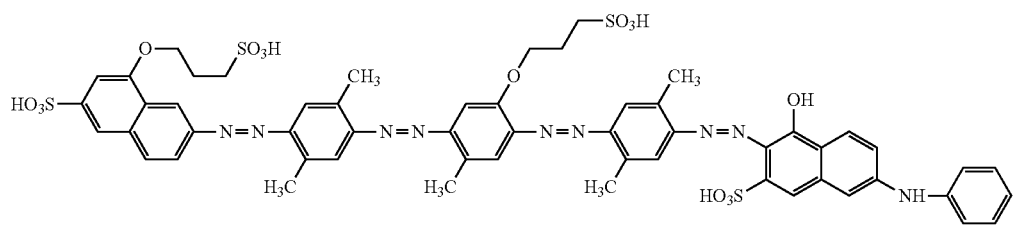 [SMILES: Cc1cc(N=Nc2cc(OCCCS(=O)(=O)O)c(N=Nc3cc(C)c(N=Nc4c(S(=O)(=O)O)cc5cc(Nc6ccccc6)ccc5c4O)cc3C)cc2C)c(C)cc1N=Nc1ccc2cc(S(=O)(=O)O)cc(OCCCS(=O)(=O)O)c2c1]

(9)

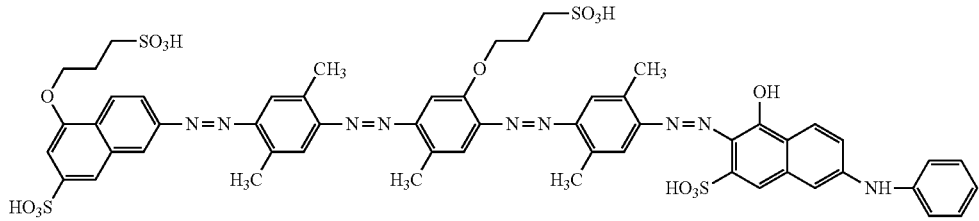 [SMILES: Cc1cc(N=Nc2cc(OCCCS(=O)(=O)O)c(N=Nc3cc(C)c(N=Nc4c(S(=O)(=O)O)cc5cc(Nc6ccccc6)ccc5c4O)cc3C)cc2C)c(C)cc1N=Nc1ccc2c(OCCCS(=O)(=O)O)cc(S(=O)(=O)O)cc2c1]

(10)

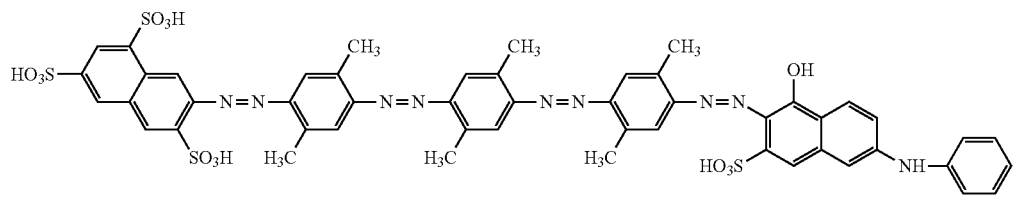 [SMILES: Cc1cc(N=Nc2cc(C)c(N=Nc3c(S(=O)(=O)O)cc4cc(Nc5ccccc5)ccc4c3O)cc2C)c(C)cc1N=Nc1cc(C)c(N=Nc2cc3c(S(=O)(=O)O)cc(S(=O)(=O)O)cc3cc2S(=O)(=O)O)cc1C]

(11)

TABLE A-continued
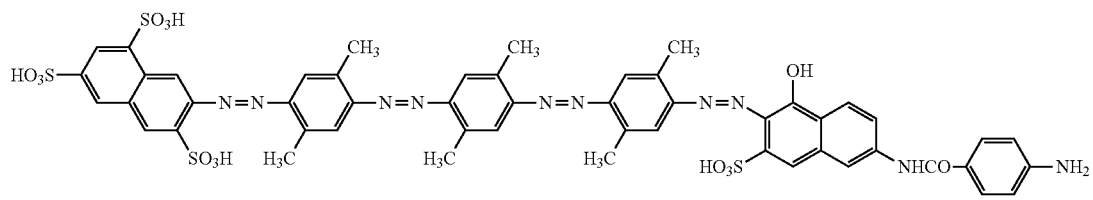
(12)
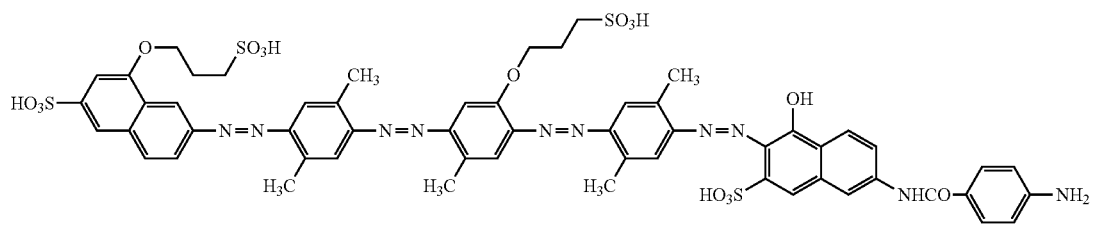
(13)
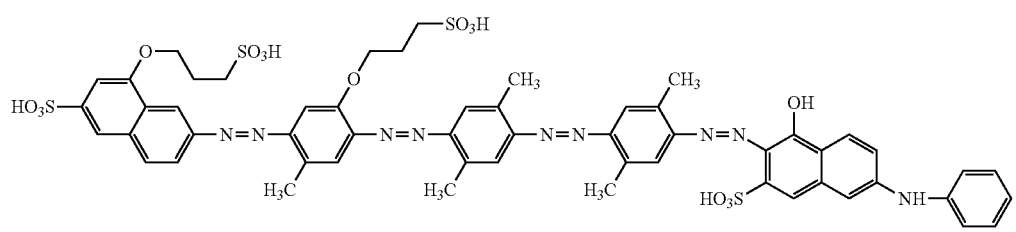 [SMILES: Cc1cc(N=Nc2cc(C)c(N=Nc3cc(C)c(N=Nc4c(S(=O)(=O)O)cc5cc(Nc6ccccc6)ccc5c4O)cc3C)cc2C)c(OCCCS(=O)(=O)O)cc1N=Nc1ccc2cc(S(=O)(=O)O)cc(OCCCS(=O)(=O)O)c2c1]
(14)
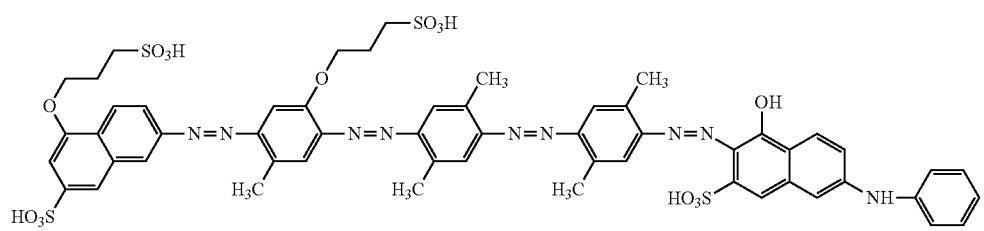 [SMILES: Cc1cc(N=Nc2cc(C)c(N=Nc3cc(C)c(N=Nc4c(S(=O)(=O)O)cc5cc(Nc6ccccc6)ccc5c4O)cc3C)cc2C)c(OCCCS(=O)(=O)O)cc1N=Nc1ccc2c(OCCCS(=O)(=O)O)cc(S(=O)(=O)O)cc2c1]
(15)
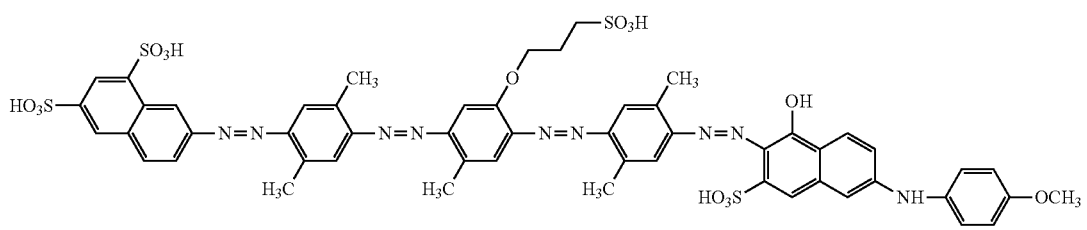 [SMILES: COc1ccc(Nc2ccc3c(O)c(N=Nc4cc(C)c(N=Nc5cc(C)c(N=Nc6cc(C)c(N=Nc7ccc8cc(S(=O)(=O)O)cc(S(=O)(=O)O)c8c7)cc6C)cc5OCCCS(=O)(=O)O)cc4C)c(S(=O)(=O)O)cc3c2)cc1]
(16)
TABLE B
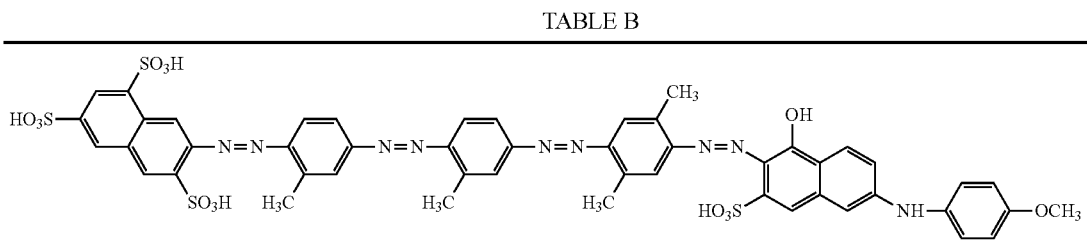
(17)
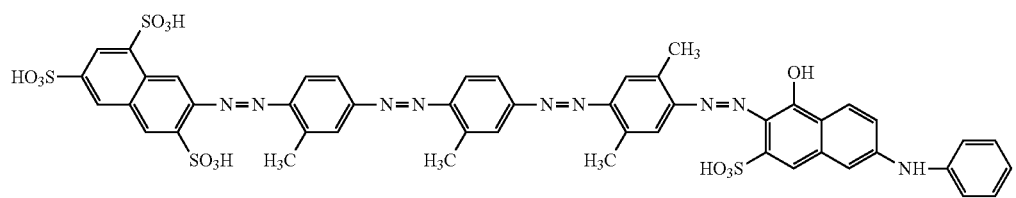
(18)

TABLE B-continued
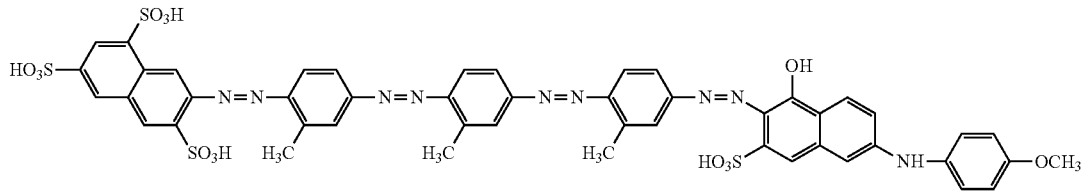 [SMILES: COc1ccc(Nc2ccc3c(O)c(N=Nc4ccc(N=Nc5ccc(N=Nc6ccc(N=Nc7cc8c(S(=O)(=O)O)cc(S(=O)(=O)O)cc8cc7S(=O)(=O)O)c(C)c6)c(C)c5)c(C)c4)c(S(=O)(=O)O)cc3c2)cc1]
(19)
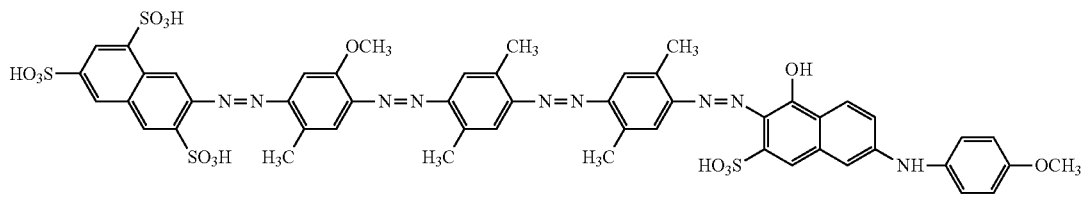 [SMILES: COc1ccc(Nc2ccc3c(O)c(N=Nc4cc(C)c(N=Nc5ccc(N=Nc6cc(C)c(N=Nc7cc8c(S(=O)(=O)O)cc(S(=O)(=O)O)cc8cc7S(=O)(=O)O)cc6OC)c(C)c5)cc4C)c(S(=O)(=O)O)cc3c2)cc1]
(20)
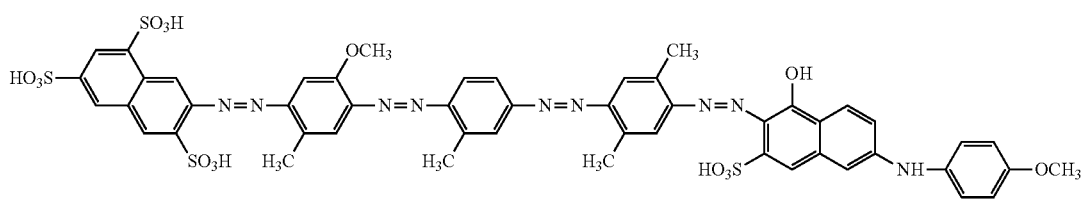
(21)
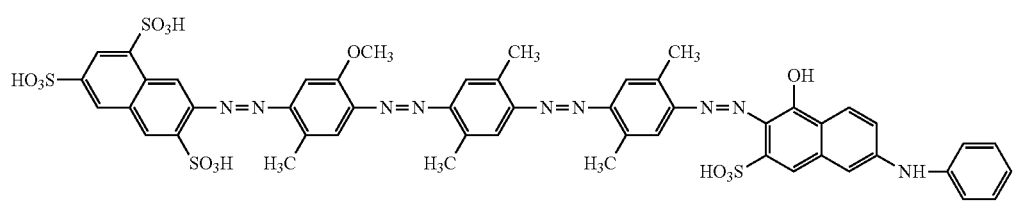 [SMILES: COc1cc(N=Nc2cc3c(S(=O)(=O)O)cc(S(=O)(=O)O)cc3cc2S(=O)(=O)O)c(C)cc1N=Nc1cc(C)c(N=Nc2cc(C)c(N=Nc3c(S(=O)(=O)O)cc4cc(Nc5ccccc5)ccc4c3O)cc2C)cc1C]
(22)
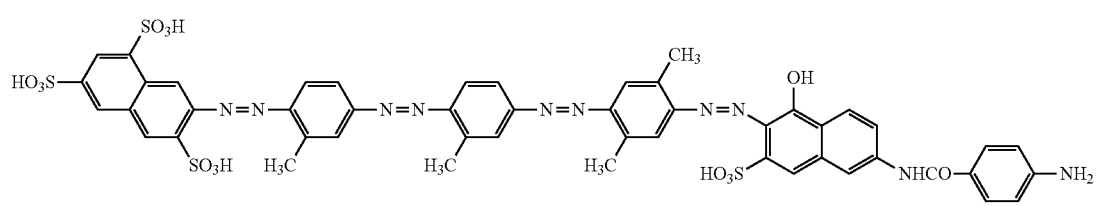
(23)
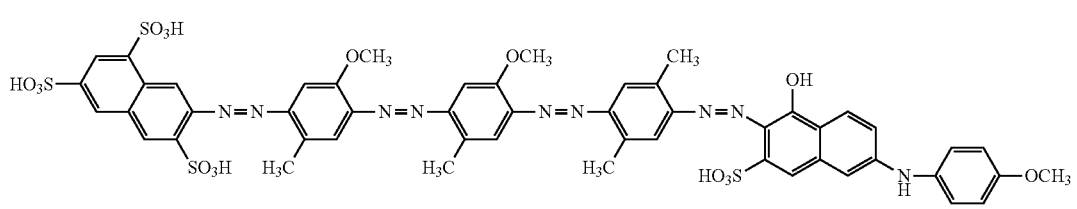 [SMILES: COc1ccc(Nc2ccc3c(O)c(N=Nc4cc(C)c(N=Nc5cc(C)c(N=Nc6cc(C)c(N=Nc7cc8c(S(=O)(=O)O)cc(S(=O)(=O)O)cc8cc7S(=O)(=O)O)cc6OC)cc5OC)cc4C)c(S(=O)(=O)O)cc3c2)cc1]
(24)
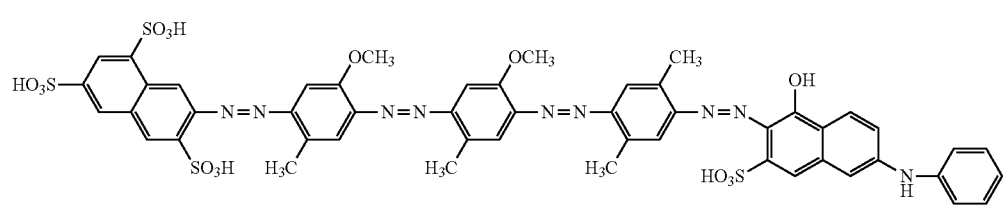 [SMILES: COc1cc(N=Nc2cc(C)c(N=Nc3cc4c(S(=O)(=O)O)cc(S(=O)(=O)O)cc4cc3S(=O)(=O)O)cc2OC)c(C)cc1N=Nc1cc(C)c(N=Nc2c(S(=O)(=O)O)cc3cc(Nc4ccccc4)ccc3c2O)cc1C]
(25)

TABLE C
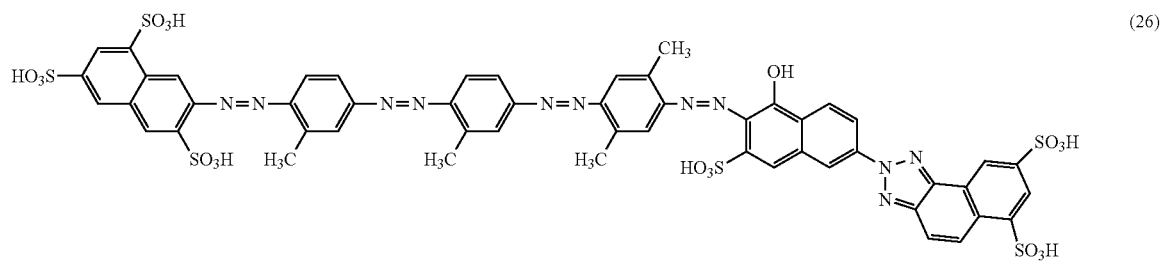
(26)
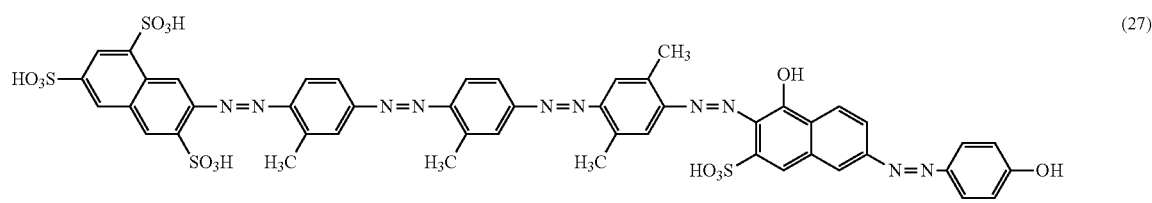
(27)
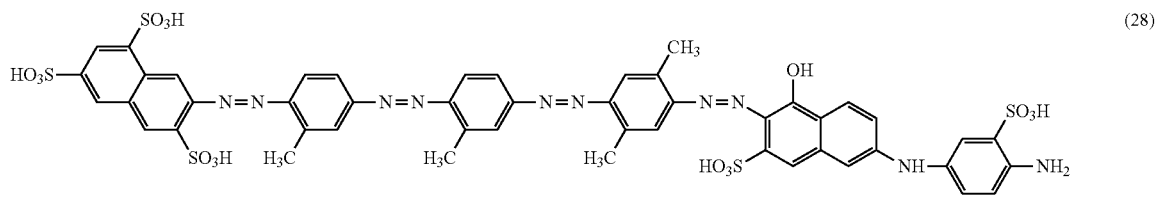
(28)
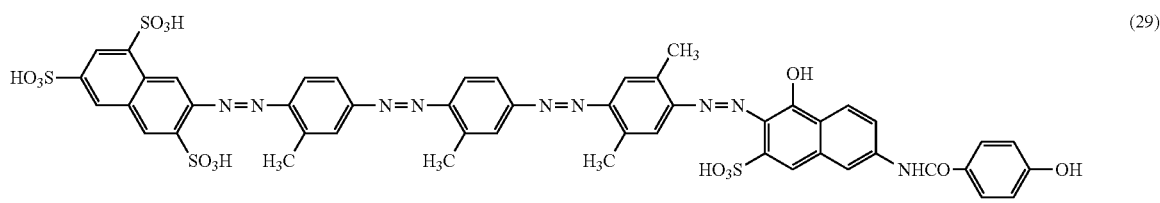
(29)
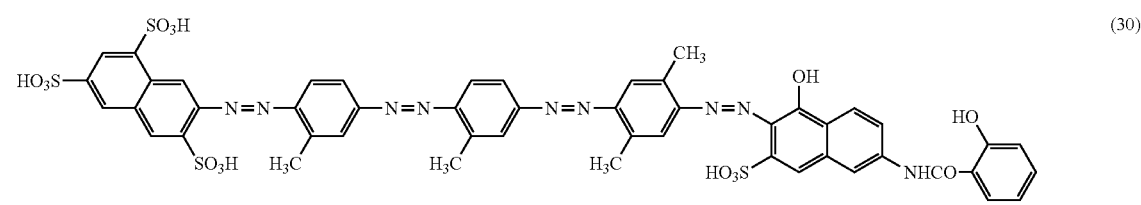
(30)
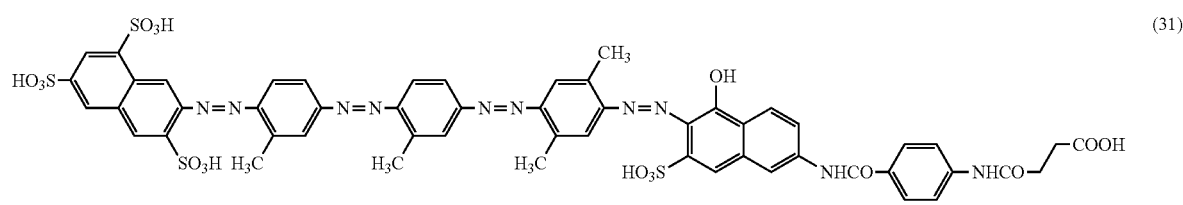
(31)
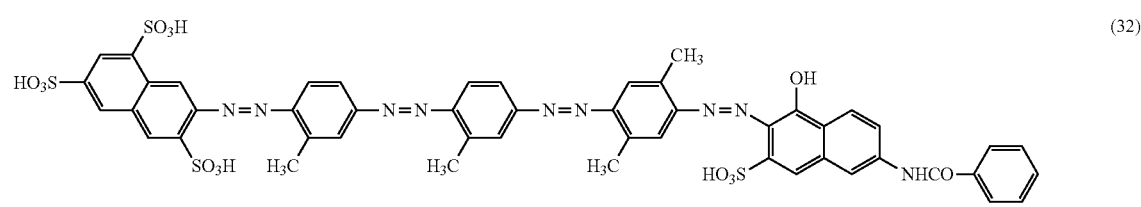
(32)

TABLE C-continued
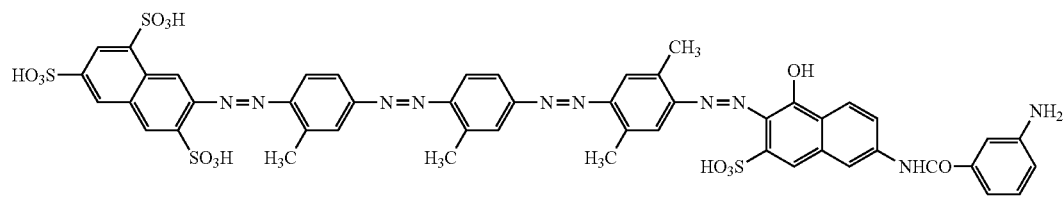
(33)
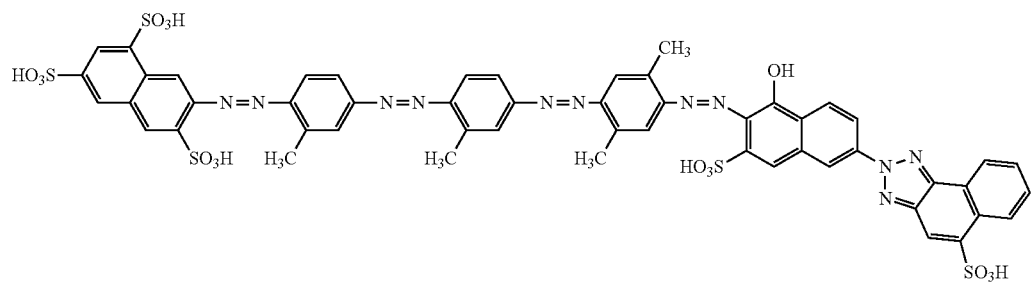 [SMILES: Cc1cc(N=Nc2cc(C)c(N=Nc3c(S(=O)(=O)O)cc4cc(-n5nc6cc(S(=O)(=O)O)c7ccccc7c6n5)ccc4c3O)cc2C)ccc1N=Nc1ccc(N=Nc2cc3c(S(=O)(=O)O)cc(S(=O)(=O)O)cc3cc2S(=O)(=O)O)c(C)c1]
(34)
TABLE D
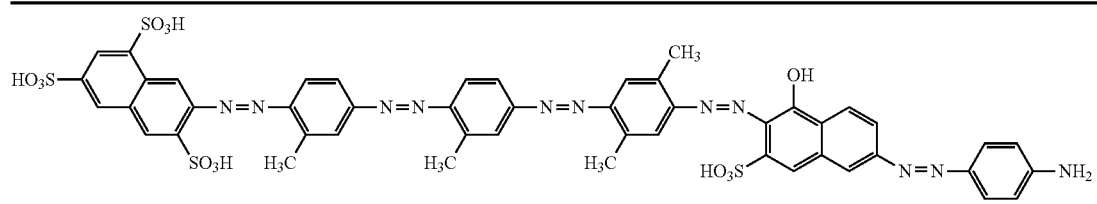
(35)
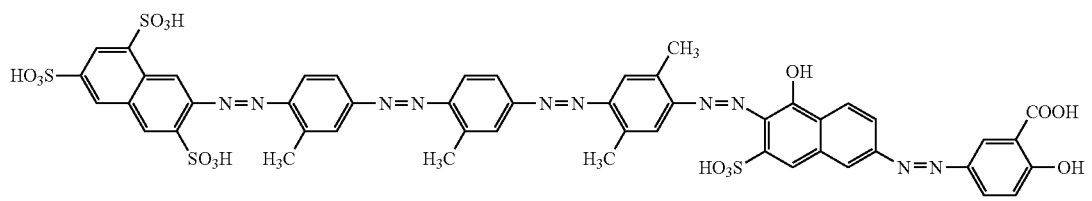 [SMILES: Cc1cc(N=Nc2cc(C)c(N=Nc3c(S(=O)(=O)O)cc4cc(N=Nc5ccc(O)c(C(=O)O)c5)ccc4c3O)cc2C)ccc1N=Nc1ccc(N=Nc2cc3c(S(=O)(=O)O)cc(S(=O)(=O)O)cc3cc2S(=O)(=O)O)c(C)c1]
(36)
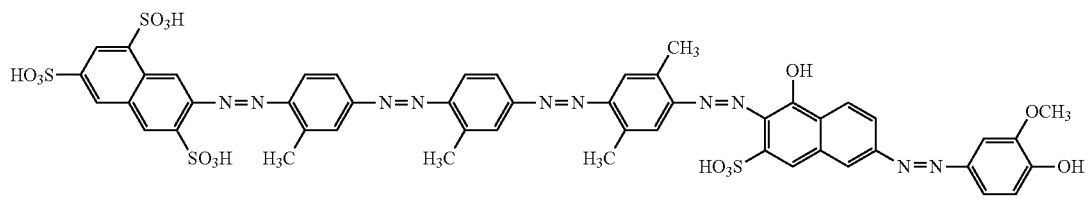 [SMILES: COc1cc(N=Nc2ccc3c(O)c(N=Nc4cc(C)c(N=Nc5ccc(N=Nc6ccc(N=Nc7cc8c(S(=O)(=O)O)cc(S(=O)(=O)O)cc8cc7S(=O)(=O)O)c(C)c6)c(C)c5)cc4C)c(S(=O)(=O)O)cc3c2)ccc1O]
(37)
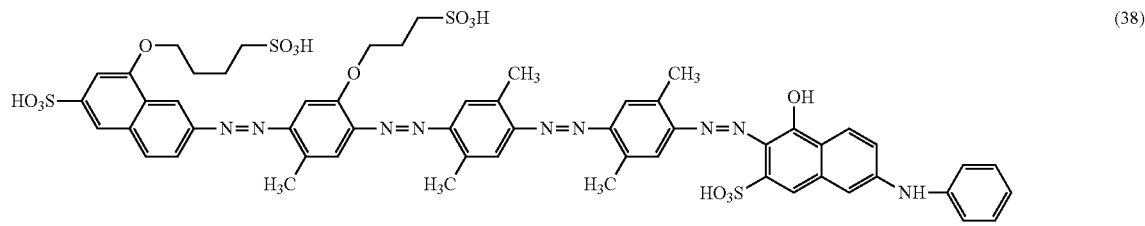
(38)
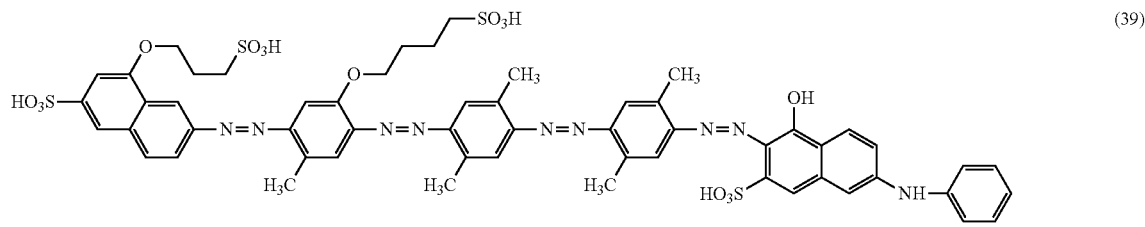
(39)

TABLE D-continued
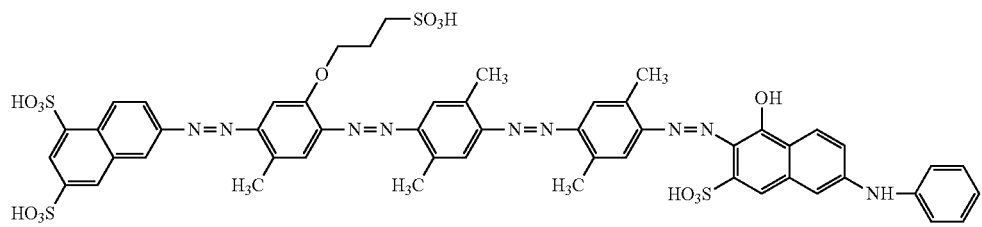 [SMILES: Cc1cc(N=Nc2cc(C)c(N=Nc3cc(C)c(N=Nc4c(S(=O)(=O)O)cc5cc(Nc6ccccc6)ccc5c4O)cc3C)cc2C)c(OCCCS(=O)(=O)O)cc1N=Nc1ccc2c(S(=O)(=O)O)cc(S(=O)(=O)O)cc2c1] (40)
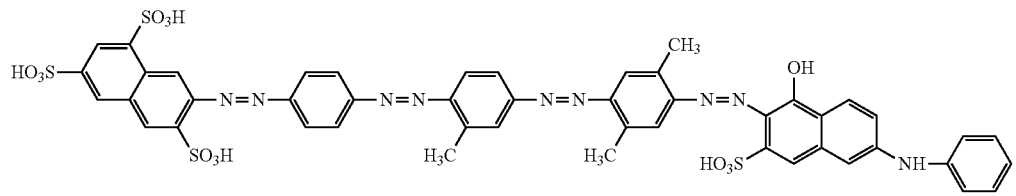 [SMILES: Cc1cc(N=Nc2cc(C)c(N=Nc3c(S(=O)(=O)O)cc4cc(Nc5ccccc5)ccc4c3O)cc2C)ccc1N=Nc1ccc(N=Nc2cc3c(S(=O)(=O)O)cc(S(=O)(=O)O)cc3cc2S(=O)(=O)O)cc1] (41)
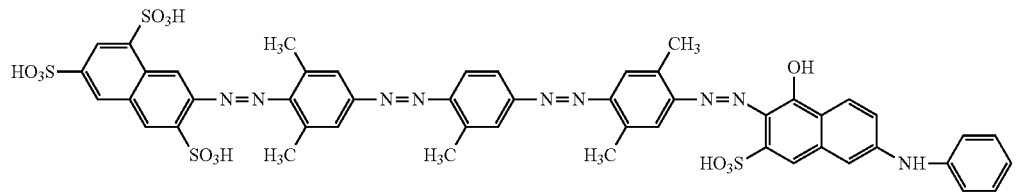 [SMILES: Cc1cc(N=Nc2cc(C)c(N=Nc3c(S(=O)(=O)O)cc4cc(Nc5ccccc5)ccc4c3O)cc2C)ccc1N=Nc1cc(C)c(N=Nc2cc3c(S(=O)(=O)O)cc(S(=O)(=O)O)cc3cc2S(=O)(=O)O)c(C)c1] (42)
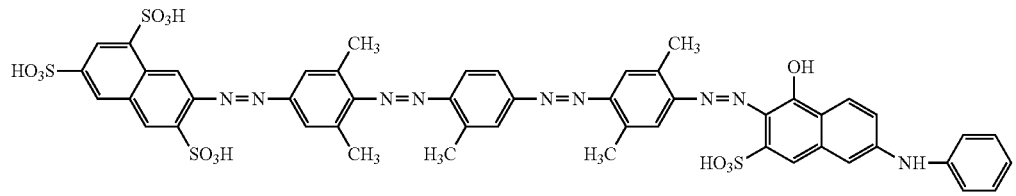 [SMILES: Cc1cc(N=Nc2c(S(=O)(=O)O)cc3cc(Nc4ccccc4)ccc3c2O)c(C)cc1N=Nc1ccc(N=Nc2c(C)cc(N=Nc3cc4c(S(=O)(=O)O)cc(S(=O)(=O)O)cc4cc3S(=O)(=O)O)cc2C)c(C)c1] (43)
TABLE E
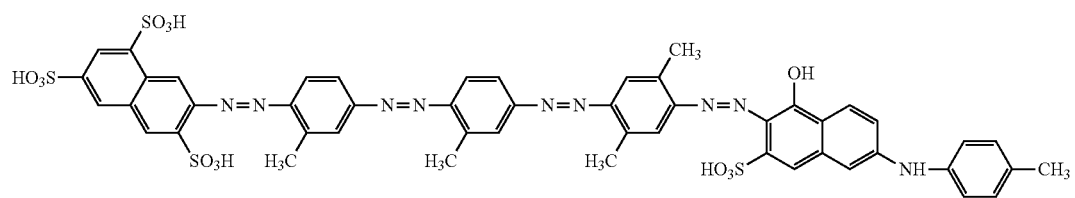 [SMILES: Cc1ccc(Nc2ccc3c(O)c(N=Nc4cc(C)c(N=Nc5ccc(N=Nc6ccc(N=Nc7cc8c(S(=O)(=O)O)cc(S(=O)(=O)O)cc8cc7S(=O)(=O)O)c(C)c6)c(C)c5)cc4C)c(S(=O)(=O)O)cc3c2)cc1] (44)
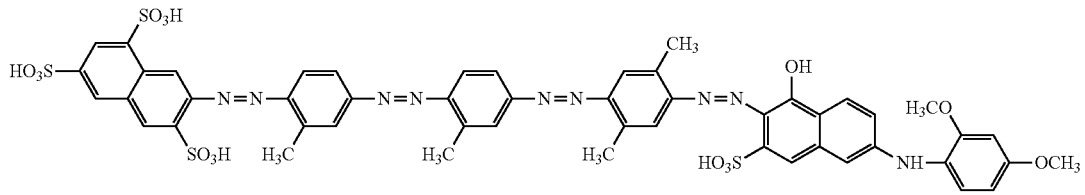 [SMILES: COc1ccc(Nc2ccc3c(O)c(N=Nc4cc(C)c(N=Nc5ccc(N=Nc6ccc(N=Nc7cc8c(S(=O)(=O)O)cc(S(=O)(=O)O)cc8cc7S(=O)(=O)O)c(C)c6)c(C)c5)cc4C)c(S(=O)(=O)O)cc3c2)c(OC)c1] (45)
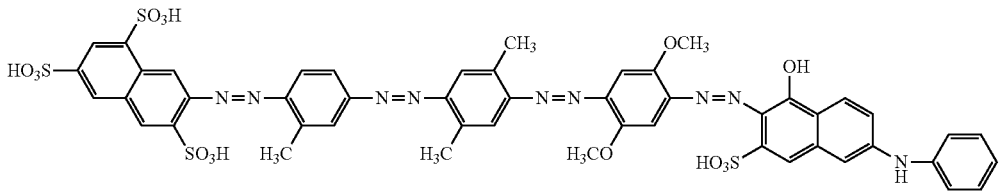 (46)

TABLE E-continued
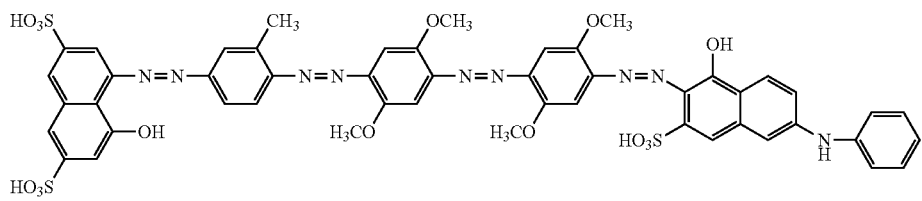 [SMILES: COc1cc(N=Nc2cc(OC)c(N=Nc3c(S(=O)(=O)O)cc4cc(Nc5ccccc5)ccc4c3O)cc2OC)c(OC)cc1N=Nc1ccc(N=Nc2cc(S(=O)(=O)O)cc3cc(S(=O)(=O)O)cc(O)c23)cc1C]
(47)
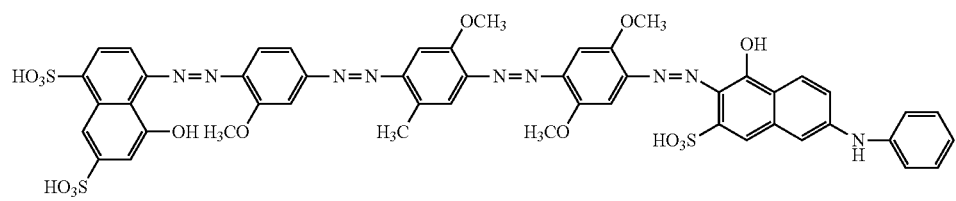 [SMILES: COc1cc(N=Nc2ccc(N=Nc3ccc(S(=O)(=O)O)c4cc(S(=O)(=O)O)cc(O)c34)c(OC)c2)c(C)cc1N=Nc1cc(OC)c(N=Nc2c(S(=O)(=O)O)cc3cc(Nc4ccccc4)ccc3c2O)cc1OC]
(48)
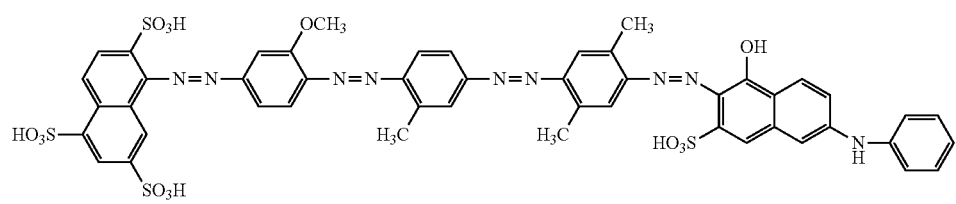 [SMILES: COc1cc(N=Nc2c(S(=O)(=O)O)ccc3c(S(=O)(=O)O)cc(S(=O)(=O)O)cc23)ccc1N=Nc1ccc(N=Nc2cc(C)c(N=Nc3c(S(=O)(=O)O)cc4cc(Nc5ccccc5)ccc4c3O)cc2C)cc1C]
(49)
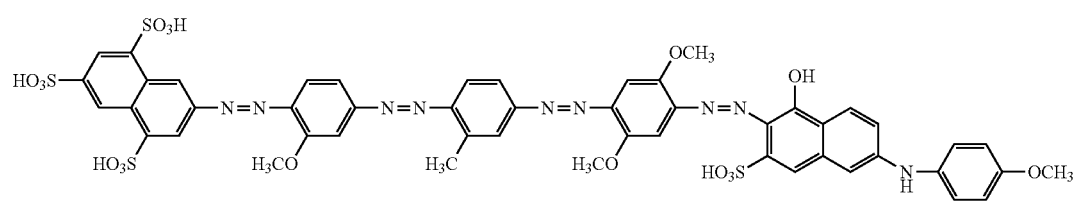 [SMILES: COc1ccc(Nc2ccc3c(O)c(N=Nc4cc(OC)c(N=Nc5ccc(N=Nc6ccc(N=Nc7cc(S(=O)(=O)O)c8cc(S(=O)(=O)O)cc(S(=O)(=O)O)c8c7)c(OC)c6)c(C)c5)cc4OC)c(S(=O)(=O)O)cc3c2)cc1]
(50)
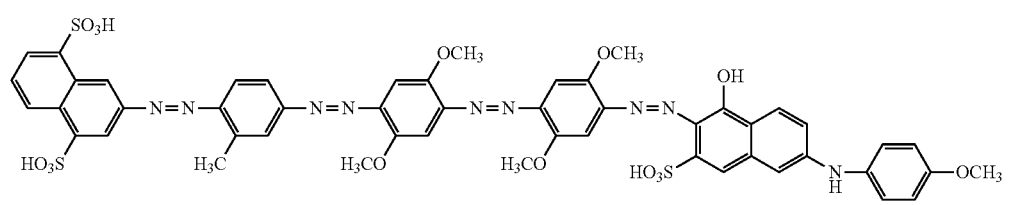 [SMILES: COc1ccc(Nc2ccc3c(O)c(N=Nc4cc(OC)c(N=Nc5cc(OC)c(N=Nc6ccc(N=Nc7cc(S(=O)(=O)O)c8cccc(S(=O)(=O)O)c8c7)c(C)c6)cc5OC)cc4OC)c(S(=O)(=O)O)cc3c2)cc1]
(51)
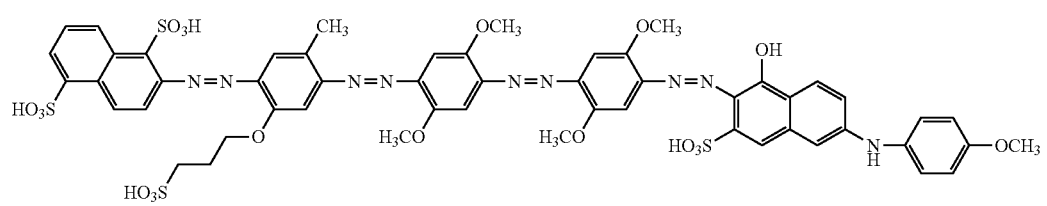 [SMILES: COc1ccc(Nc2ccc3c(O)c(N=Nc4cc(OC)c(N=Nc5cc(OC)c(N=Nc6cc(OCCCS(=O)(=O)O)c(N=Nc7ccc8c(S(=O)(=O)O)cccc8c7S(=O)(=O)O)cc6C)cc5OC)cc4OC)c(S(=O)(=O)O)cc3c2)cc1]
(52)
TABLE F
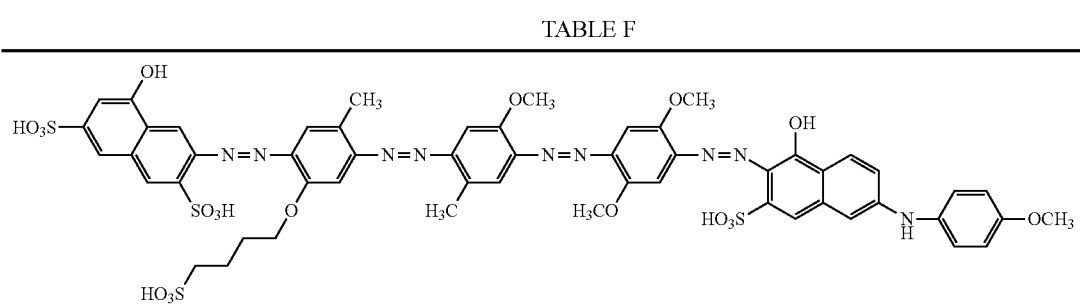
(53)

TABLE F-continued
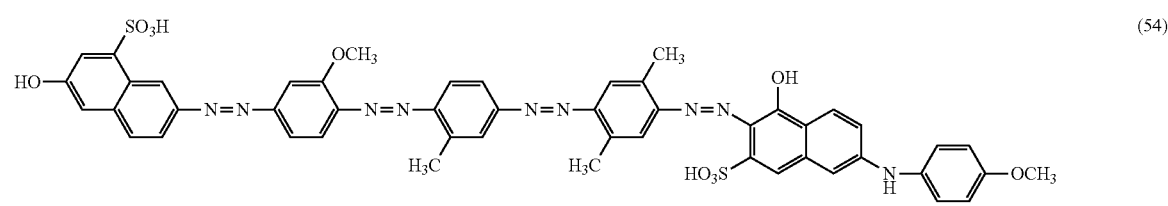 (54)
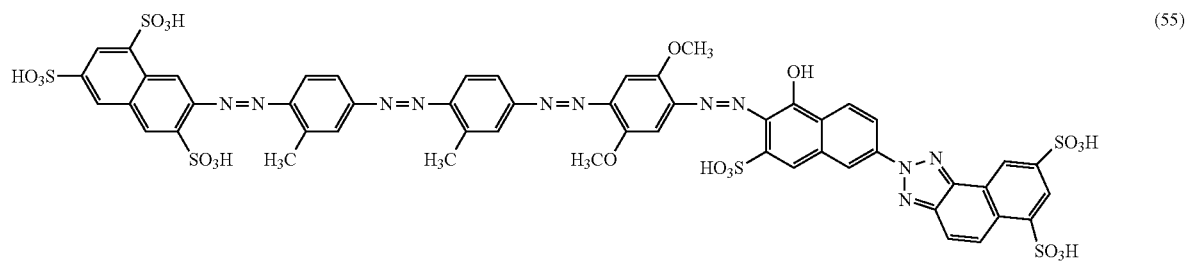 (55)
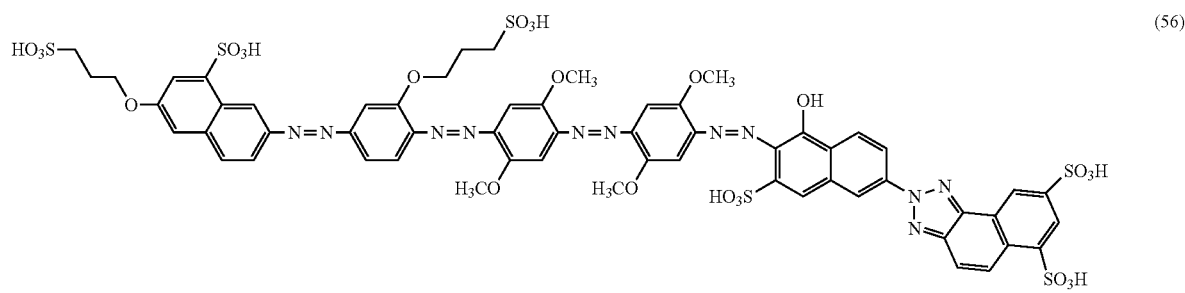 (56)
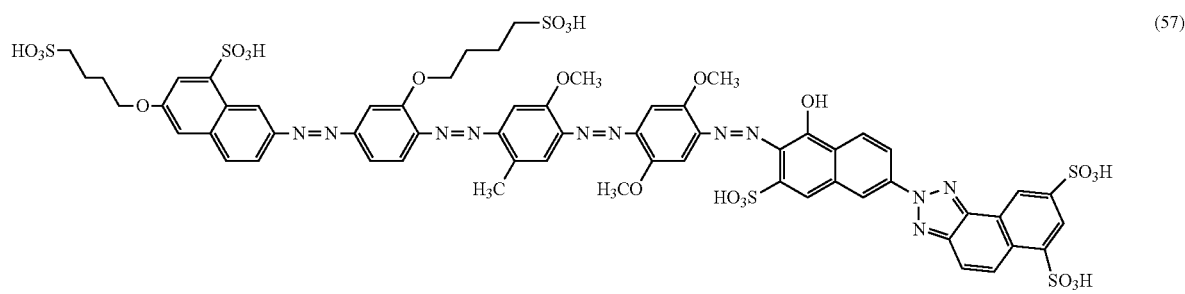 (57)
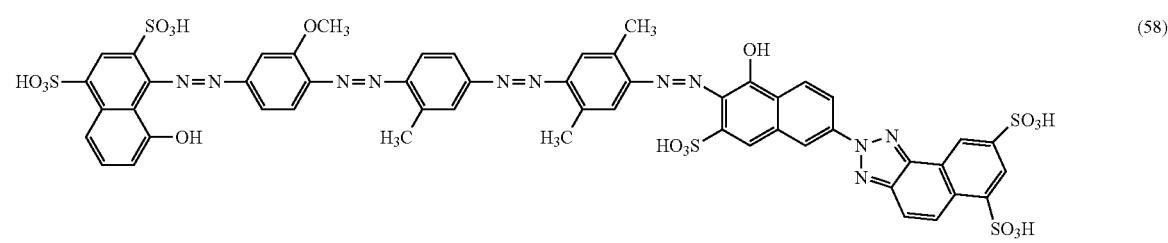 (58)
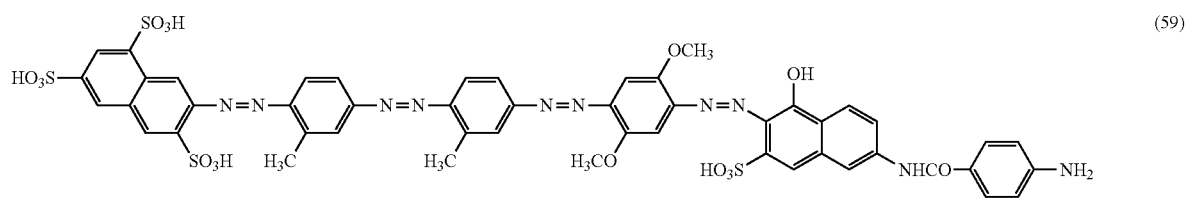 (59)

TABLE F-continued
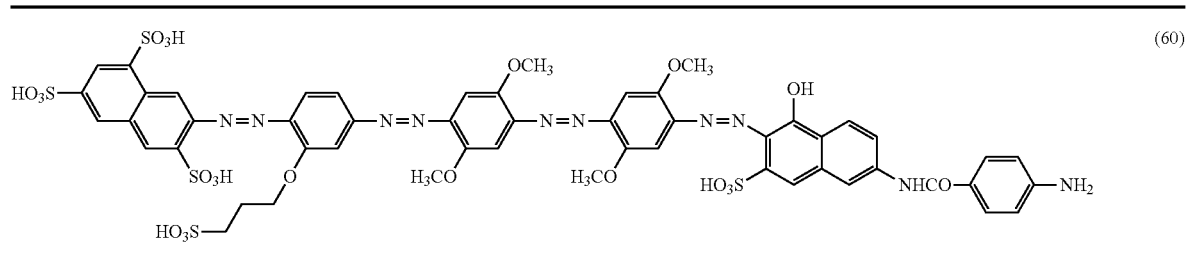
(60)
TABLE G
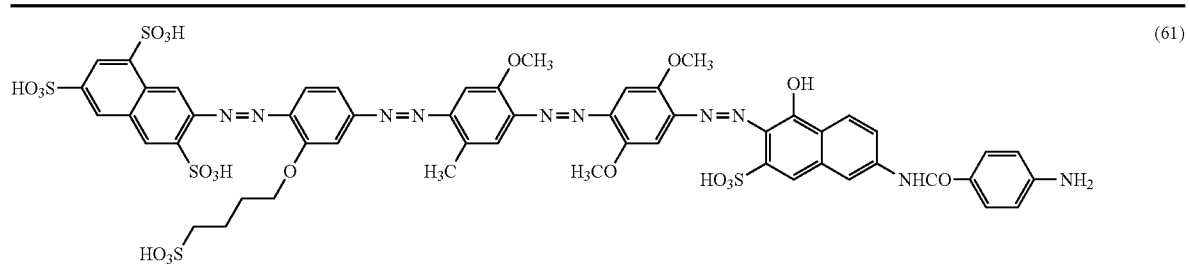
(61)
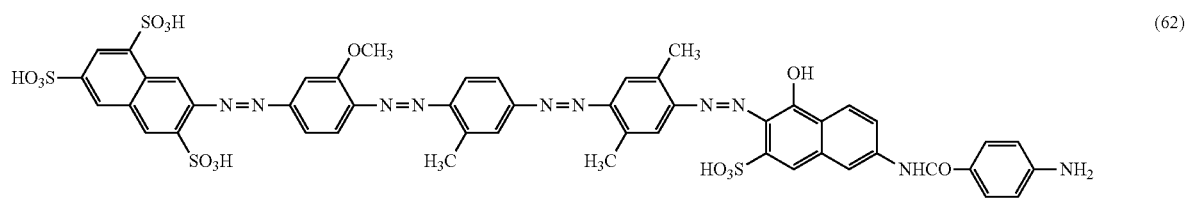
(62)
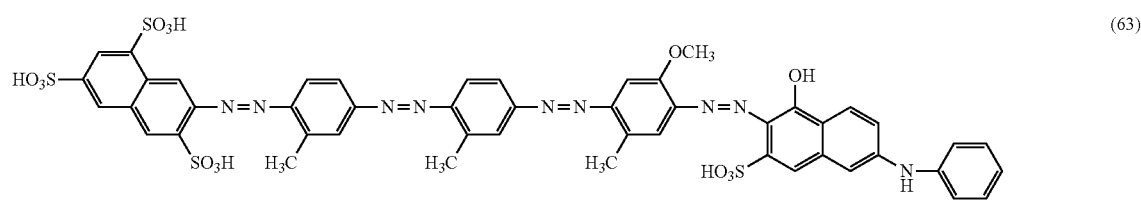
(63)
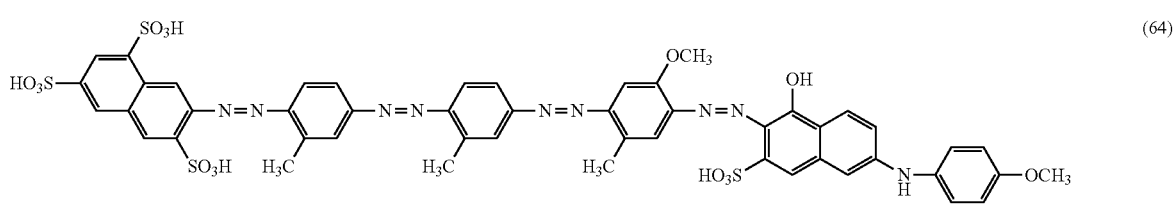
(64)
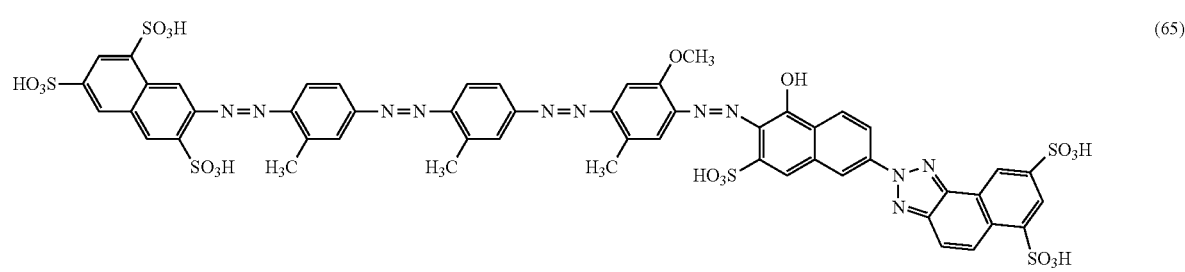
(65)

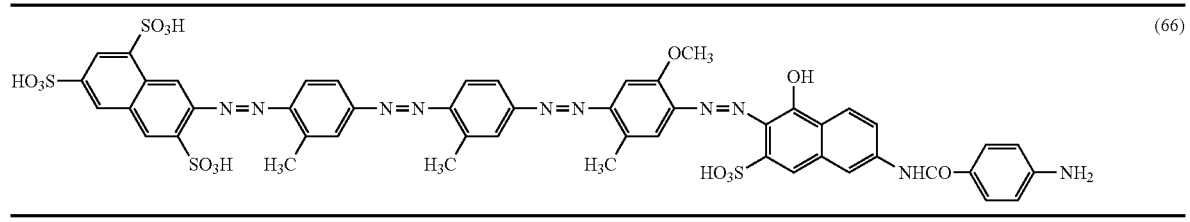
(66)

The azo compound represented by the above formula (1) and a salt thereof can be easily manufactured by conducting known diazotization and coupling in accordance with a usual azo dye-manufacturing method as described in Non-Patent Literature 1.

A specific manufacturing method includes, for example, the below-described manufacturing method.

A compound (hereinafter, referred to as a starting material, for simplicity) to be a starting material for synthesis of an azo compound represented by the formula (1) or a salt thereof of the present invention is a naphthylamine compound corresponding to a naphthyl group represented by A in the above formula (1), and it includes, for example, naphthylamine sulfonic acids, or sulfoalkoxynaphthylamine sulfonic acids obtained by sulfoalkylation of aminonaphtholsulfonic acids in accordance with a manufacturing method described in Patent Literature 8, page 35, lines 35 to 39, or the like. A compound corresponding to a naphthyl group represented by A in the above formula (1) is diazotized, followed by primary coupling with an aniline of the following formula (A) to obtain a monoazoamino compound represented by the following formula (B).

Formula (A)

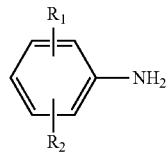
(A)

in the formula (A), $R_1$ and $R_2$ have the same meanings as $R_1$ and $R_2$ in the above formula (1).

Formula (B)

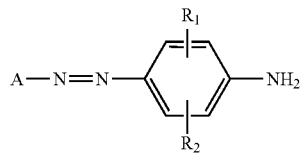
(B)

In the formula (B), A, $R_1$ and $R_2$ have the same meanings as A, $R_1$ and $R_2$ in the above formula (1).

Subsequently, this monoazoamino compound (B) is diazotized, followed by secondary coupling with an aniline of the following formula (C) to obtain a disazoamino compound represented by the following formula (D).

Formula (C)

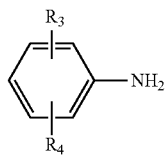
(C)

In the formula (C), $R_3$ and $R_4$ have the same meanings as $R_3$ and $R_4$ in the above formula (1).

Formula (D)

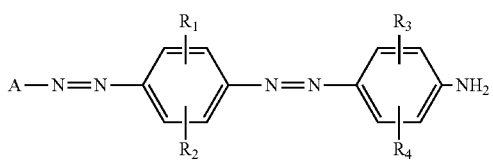
(D)

In the formula (D), A and $R_1$ to $R_4$ have the same meanings as A and $R_1$ to $R_4$ in the above formula (1).

This disazoamino compound is diazotized, followed by tertiary coupling with an aniline of the following formula (E) to obtain a trisazoamino compound represented by the following formula (F).

Formula (E)

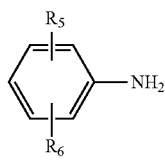
(E)

In the formula (E), $R_5$ and $R_6$ have the same meanings as $R_5$ and $R_6$ in the above formula (1).

Formula (F)

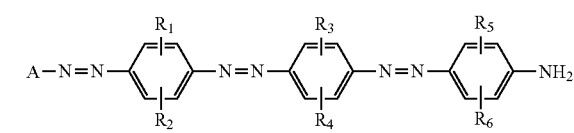
(F)

In the formula (F), A and $R_1$ to $R_6$ have the same meanings A and $R_1$ to $R_6$ in the above formula (1).

This trisazoamino compound is diazotized, followed by quaternary coupling with a naphthol represented by the following formula (G) to obtain an azo compound of the above formula (1).

Formula (G)

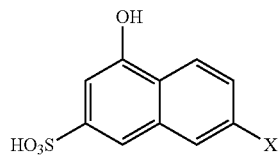

(G)

In the formula (G), X has the same meaning as X in the above formula (1).

In the above-described reaction, diazotization process is carried out by a forward method in which a nitrite salt such as sodium nitrite is mixed with a solution or suspension of a diazo component in aqueous mineral acid solution such as hydrochloric acid, sulfuric acid and the like, or by a reverse method in which a nitrite salt is added to an aqueous neutral or weak alkaline solution of a diazo component, and this mixture is mixed with mineral acid. The diazotization temperature is appropriately −10 to 40° C. Meanwhile, the coupling processes with anilines are carried out by mixing each diazo solution described above with an aqueous acidic solution such as hydrochloric acid, acetic acid and the like at a temperature of −10 to 40° C. under an acidic condition of pH 2 to 7.

The monoazo compound, the disazo compound and the trisazo compound obtained by coupling can be taken out by filtration, according to necessity, after the solution or suspension after reaction is precipitated by aciding out or salting out. The solution or suspension after each coupling reaction can be also used in next process as it is. In the case of a suspension of an insoluble diazonium salt, the suspension can be also filtered and used as a press cake in next coupling process.

Among anilines represented by the formulas (A), (C) and (E) which are used for the primary, secondary and tertiary couplings, a specific method of manufacturing anilines having an alkoxy group substituted with a sulfo group as $R_1$ to $R_6$ can include a method in which sulfoalkoxyanilines are manufactured by sulfoalkylation and reduction of phenols in accordance with the manufacturing method described in Patent Literature 8, page 35, lines 35 to 39.

The quaternary coupling reaction of a diazotized compound of a trisazoamino compound with a naphthol represented by the formula (G) is carried out at a temperature of −10 to 40° C. under a neutral to alkaline condition of pH 7 to 10. After completion of reaction, the product is precipitated by salting out and filtered to take out. In addition, when purification is required, salting out may be repeated or precipitation from the reaction liquid may be conducted using an organic solvent. The organic solvent used for purification includes a water-soluble organic solvent, for example, alcohols such as methanol and ethanol, and ketones such as acetone, and the like.

In this regard, in the present invention, the azo compound represented by the above formula (1) is used as a free acid, and in addition, it can be used as a salt of the azo compound. Such a salt includes alkali metal salts such as lithium salt, sodium salt and potassium salt, an ammonium salt, and organic salts such as amine salt. In general, a sodium salt is used.

The starting material for synthesis of the azo compound represented by the above formula (1) or a salt thereof is a naphthylamine compound corresponding to a substituted-naphthyl group represented by A. The substituent in said naphthylamine compound to be a starting material includes, specifically, a sulfo group, a hydroxy group, a tosylated hydroxy group, an amino group, a substituted amino group, a nitro group, a substituted amide group, a lower alkoxy group having a sulfo group, or the like, and it is preferably a sulfo group, a hydroxy group, or a lower alkoxy group having a sulfo group, and more preferably a sulfo group, or a lower alkoxy group having a sulfo group. The lower alkoxy group having a sulfo group is preferably a straight-chain lower alkoxy having a sulfo group, and above all, it is preferred that the substitution position of the sulfo group is a terminal of the alkoxy group. Here, the lower alkoxy group refers to an alkoxy group having a carbon atom number of 1 to 5. The lower alkoxy group having a sulfo group is preferably either a 3-sulfopropoxy group or a 4-sulfobutoxy group.

When the azo compound where A is a group represented by the above formula (6) is synthesized, n as the substituent number of the sulfo group in the naphthylamine compound corresponding to the above formula (6) is 1 to 3. In the naphthylamine compound corresponding to the above formula (6), the position of the sulfo group may be in any either benzene nuclei in the naphthalene ring. The preferable substitution position of the sulfo group is any of the 1-position, the 3-position and the 6-position when the position of the amino group is the 7-position, and when a plurality of sulfo groups are present, the preferable substitution positions of the sulfo groups are also in any combination of the 1-position, the 3-position and the 6-position.

The naphthylamine compound corresponding to the substituted-naphthyl group represented by A includes, for example, 2-aminonaphthalene-1-sulfonic acid, 8-aminonaphthalene-1-sulfonic acid, 5-aminonaphthalene-1-sulfonic acid, 5-aminonaphthalene-2-sulfonic acid, 8-aminonaphthalene-2-sulfonic acid, 3-aminonaphthalene-1-sulfonic acid, 6-aminonaphthalene-2-sulfonic acid, 4-aminonaphthalene-1-sulfonic acid, 7-aminonaphthalene-1,3-disulfonic acid, 6-aminonaphthalene-1,3-disulfonic acid, 3-amino-7-nitronaphthalene-1,5-disulfonic acid, 4-aminonaphthalene-1,6-disulfonic acid, 4-aminonaphthalene-1,5-disulfonic acid, 5-aminonaphthalene-1,3-disulfonic acid, 3-aminonaphthalene-1,5-disulfonic acid, 2-aminonaphthalene-1,5-disulfonic acid, 4-aminonaphthalene-1,6-disulfonic acid, 7-aminonaphthalene-1,3,6-trisulfonic acid, 7-aminonaphthalene-1,3,5-trisulfonic acid, 8-aminonaphthalene-1,3,6-trisulfonic acid, 5-aminonaphthalene-1,3,6-trisulfonic acid, 7-amino-3-(3-sulfopropoxy)naphthalene-1-sulfonic acid, 7-amino-3-(4-sulfobutoxy)naphthalene-1-sulfonic add, 7-amino-4-(3-sulfopropoxy)naphthalene-2-sulfonic acid, 7-amino-4-(4-sulfobutoxy)naphthalene-2-sulfonic acid, 6-amino-4-(3-sulfopropoxy)naphthalene-2-sulfonic acid, 6-amino-4-(4-sulfobutoxy)naphthalene-2-sulfonic acid, 2-amino-5-(3-sulfopropoxy)naphthalene-1,7-disulfonic acid, 6-amino-4-(3-sulfopropoxy)naphthalene-2,7-disulfonic acid, 7-amino-3-(3-sulfopropoxy)naphthalene-1,5-disulfonic acid, or the like. Preferable are 7-aminonaphthalene-1,3-disulfonic acid, 6-aminonaphthalene-1,3-disulfonic acid, 7-aminonaphthalene-1,3,6-trisulfonic acid, 7-amino-4-(3-sulfopropoxy) naphthalene-2-sulfonic acid or 6-amino-4-(3-sulfopropoxy) naphthalene-2-sulfonic acid, and particularly preferable are 7-aminonaphthalene-1,3-disulfonic acid, 7-aminonaphthalene-1,3,6-trisulfonic acid or 7-amino-4-(3-sulfopropoxy) naphthalene-2-sulfonic acid.

The substituents $R_1$ to $R_6$ in the anilines represented by the formulas (A), (C) and (E) which are primary, secondary and tertiary coupling components (also referred to as coupler) each independently represent a hydrogen atom, a lower alkyl group, a lower alkoxy group, a sulfo group, or a lower alkoxy group having a sulfo group. Preferable $R_1$ to $R_6$ are a hydrogen atom, a methyl group, a methoxy group, or a 3-sulfopropoxy group or a 4-sulfobutoxy group, and more preferable $R_1$ to $R_6$ are a hydrogen atom, a methyl group, a methoxy group or a 3-sulfopropoxy group. One or two of these substituents may be bonded. The bonding position for $R_1$ to $R_6$ is the 2-position only, the 3-position only, the 2- and 5-positions, the 3- and 5-positions or the 2- and 6-positions, relative to each amino group of anilines, and the 3-position only or the 2- and 5-positions are preferable. In this regard, "the 2-position only" or "the 3-position only" means that only the 2-position or the 3-position has one substituent other than a hydrogen atom.

Specific examples of said anilines where $R_1$ to $R_6$ are lower alkoxy groups having a sulfo group include 3-(2-amino-4-methylphenoxy)propane-1-sulfonic acid, 3-(2-aminophenoxy)propane-1-sulfonic acid, 3-(2-amino-4-methylphenoxy)butane-1-sulfonic acid and the like. Specific examples of anilines other than them, for example, aniline, 2-methylaniline, 3-methylaniline, 2-ethylaniline, 3-ethylaniline, 2,5-dimethylaniline, 2,5-diethylaniline, 2-methoxyaniline, 3-methoxyaniline, 2-methoxy-5-methylaniline, 2,5-dimethoxyaniline, 3,5-dimethylaniline, 2,6-dimethylaniline, 3,5-dimethoxyaniline or the like. The amino group of these anilines may be protected. The protecting group includes, for example, its omega-methanesulfo group.

An aniline represented by the formula (A) used in the primary coupling, an aniline represented by the formula (C) used in the secondary coupling and/or an aniline represented by the formula (E) used in the tertiary coupling may be the same or different from each other.

X in a naphthol represented by the formula (G) which is a quaternary coupling component (coupler) is the same as X in the above formula (1), and preferably a phenylamino group having a substituent, a benzoylamino group having a substituent, a phenylazo group having a substituent, or a naphthotriazole group having a substituent. These substituents are preferably a hydrogen atoms, lower alkyl groups, lower alkoxy groups, hydroxy groups, carboxy groups, sulfo groups, amino groups or substituted amino groups.

In the case where X in the formula (G) is a phenylamino group having a substituent, it is preferred that X is a phenylamino group having $R_7$ and $R_8$ represented by the above formula (2). $R_7$ and $R_8$ each independently represent a hydrogen atom, a methyl group, a methoxy group, a sulfo group, an amino group or a substituted amino group, and are more preferably a hydrogen atom, a methyl group, a methoxy group or an amino group, in addition, it is more preferred that at least one substituent of $R_7$ and $R_8$ is in the p-position relative to the amino group.

In the case where X in the formula (G) is a benzoylamino group having a substituent, it is preferred that X is a benzoylamino group having $R_9$ represented by the above formula (3). $R_9$ represents a hydrogen atom, a hydroxy group, an amino group or a substituted amino group, and is preferably a hydrogen atom, an amino group or a substituted amino group and more preferably an amino group. It is more preferred that the substitution position of $R_9$ is the p-position.

In the case where X in the formula (G) is a naphthotriazole group having a substituent, it is preferred that X is a naphthotriazole group having a sulfo group represented by the above formula (4). In the above formula (4), m represents 1 or 2 and is preferably 2.

In the case where X in the formula (G) is a phenylazo group having a substituent, it is preferably a phenylazo group having $R_{10}$ to $R_{12}$ represented by the above formula (5). $R_{10}$ to $R_{12}$ each independently represent a hydrogen atom, a hydroxy group, a lower alkyl group, a lower alkoxy group, an amino group or a substituted amino group. It is preferred that at least one of $R_{10}$ to $R_{12}$ is a substituent other than a hydrogen atom, and said substituent other than a hydrogen atom is more preferably a hydroxy group, an amino group, or a substituted amino group and particularly preferably a hydroxy group.

It is preferred that a naphthol represented by the formula (G) which is a quaternary coupling component is a group where X is represented by any of the above formulas (2) to (5), and it is more preferred that a substituent in the above formulas (2) to (5) is a preferable substituent described above.

Specific examples of naphthols represented by the formula (G) can include 7-aminonaphthalene-1,3,6-trisulfonic acid, 6-(4'-methoxyphenylamino)-1-naphthol-3-sulfonic acid, 6-(4'-aminobenzoylamino)-1-naphthol-3-sulfonic acid, 6-(disulfonaphtholtriazole)-1-naphthol-3-sulfonic acid represented by the later-described formula (70), 6-(4'-hydroxyphenylazo)-3-sulfo-1-naphthol, 6-phenylamino-1-naphthol-3-sulfonic acid, 6-phenylamino-1-naphthol-3-sulfonic acid or the like.

In the dye-based polarizing film or the dye-based polarizing plate of the present invention, the azo compound represented by the above formula (1) or a salt thereof is used alone or in combination of a plurality thereof. In the dye-based polarizing film or the dye-based polarizing plate of the present invention, one or more kinds of organic dyes other than the azo compound or represented by the above formula (1) or a salt thereof may be used in combination according to necessity. The organic dye to be used in combination is not particularly limited, it is preferably a dye having absorption characteristics in a wavelength region different from the absorption wavelength region of the azo compound or a salt thereof of the present invention and having high dichroism. Typical examples thereof include, for example, C.I. Direct Yellow 12, C.I. Direct Yellow 28, C.I. Direct Yellow 44, C.I. Direct Orange 26, C.I. Direct Orange 39, C.I. Direct Orange 71, C.I. Direct Orange 107, C.I. Direct Red 2, C.I. Direct Red 31, C.I. Direct Red 79, C.I. Direct Red 81, C.I. Direct Red 247, C.I. Direct Green 80, C.I. Direct Green 59, the dyes described in Patent Literatures 1 to 7, and the like. It is more preferred to use a dye developed for such polarizing plates as described in Patent Literatures 1 to 7, according to the purpose. These coloring matters are used as a free acid or as an alkali metal salt (for example, Na salt, K salt, Li salt), an ammonium salt or a salt of an amines.

In the case where another organic dye is used in combination according to necessity, the kind of dye to be mixed varies depending on the intended polarizing film which is any of a neutral color polarizing film, a color polarizing film for a liquid crystal projector or another color polarizing film, respectively. The mixing ratio is not particularly limited but it is preferred to use at least one or more kinds of the above-described organic dyes generally in the range of 0.1 to 10 parts by mass in all, on the basis of the mass of the azo compound of the above formula (1) and a salt thereof.

By allowing the azo compound represented by the above formula (1) or a salt thereof along with another dichroic dye according to necessity to be contained in a polarizing raw film material (for example, polymer film) and then by orientation of the azo compound or a salt thereof of the present invention by a known method; or by mixing with a liquid crystal or by orientation of the azo compound or a salt thereof of the present invention by a known coating method, each kind of color polarizing film or a polarizing film having neutral color can be manufactured.

At least one surface of the obtained polarizing film can be provided with a transparent protective film to give a polarizing plate of the present invention. In addition, the polarizing plate of the present invention can be also provided with a protective layer or an AR (antireflection) layer and a support, and the like, according to necessity. The thus-obtained polarizing plate of the present invention is used for liquid crystal projectors, electronic calculators, clocks, laptop personal computers, word processors, liquid crystal televisions, car navigation systems and indoor-outdoor measuring instruments, indicators and the like, lenses and glasses.

The polarizing raw base material (polymer film) used for the dye-based polarizing film of the present invention is preferably a film comprising a polyvinyl alcohol resin or a derivative thereof (for example, vinyl alcohol copolymer resin, modified form of polyvinyl alcohol resin, or the like). Their specific examples include polyvinyl alcohol obtained by saponification of polyvinyl acetate, or a vinyl alcohol copolymer (preferably one containing 50% or more of a vinyl alcohol component) obtained by saponification of a copolymer of acetic acid vinyl with another copolymerizable monomer, for example, C2-C3 olefins such as ethylene and propylene and C3-C4 unsaturated carboxylic acids such as crotonic acid, acrylic acid, methacrylic acid and maleic acid; polyvinyl formal or polyvinyl acetal obtained by modification of polyvinyl alcohol with formaldehyde, acetaldehyde or the like; and the like. Above all, a polyvinyl alcohol film is suitably used in terms of dye adsorptivity and orientation property. The thickness of said base material is usually 30 to 100 μm and preferably approximately 50 to 80 μm.

In order to allow the azo compound of the above formula (1) or a salt thereof to be contained in such a polarizing raw base material (polymer film), a method of dyeing a polymer film is usually employed. The dyeing is conducted, for example, as follows. First, the azo compound or a salt thereof of the present invention, and if necessary, another dichroic dye (hereinafter, both together also referred to as "water-soluble dye") are dissolved in water to prepare a dye bath. The dye concentration in the dye bath is not particularly limited but usually selected in the range of approximately 0.001 to 10% by mass. In addition, a dyeing auxiliary agent may be used for the dye bath, if necessary. The dyeing auxiliary agent includes, for example, a sodium sulfate. The dyeing auxiliary agent is suitably used at a concentration of approximately 0.1 to 10% by mass in the dye bath. In the thus-prepared dye bath, a polymer film is immersed for 1 to 10 minutes to conduct dyeing. The dyeing temperature is preferably, approximately 40 to 80° C.

The orientation of the azo compound of the above formula (1) or a salt thereof is conducted by stretching a polymer film dyed as described above. As a method of stretching, any known method may be used, for example, a wet method, a dry method and the like. The polymer film stretching may be also conducted before dyeing in some cases. In this case, the water-soluble dye orientation is conducted at the time of dyeing.

To the polymer film obtained by allowing a water-soluble dye to be contained followed by orientation, an after-treatment such as boric acid treatment is applied by a known method, according to necessity. Such an after-treatment is conducted for the purpose of improving the light ray transmittance and degree of polarization of a polarizing film. The conditions of boric acid treatment vary depending on the kind of polymer film used and the kind of dye used, but generally, the boric acid concentration of an aqueous boric acid solution is in the range of 0.1 to 15% by mass and preferably 1 to 10% by mass and the treatment is conducted by immersion at a temperature ranging from 30 to 80° C. and preferably from 40 to 75° C. for 0.5 to 10 minutes. In addition, fixing treatment may be additionally conducted with an aqueous solution containing a cation-based polymer compound, according to necessity.

To either or both of the surfaces of the thus-obtained dye-based polarizing film of the present invention, a transparent protective film excellent in optical transparency and mechanical strength can be attached to give a polarizing plate. As a material to form a protective film, for example, a cellulose acetate-based film, an acrylic-based film, a fluorine-based film like an ethylene tetrafluoride/propylene hexafluoride-based copolymer, a film comprising a polyester resin, a polyolefin resin or a polyamide-based resin, or the like is used. Preferably, a triacetyl cellulose (TAC) film or a cycloolefin-based film is used. The protective film thickness is usually 40 to 200 μm.

The adhesive which can be used to attach a polarizing film to a protective film includes a polyvinyl alcohol-based adhesive, a urethane emulsion-based adhesive, an acrylic-based adhesive, a polyester-isocyanate-based adhesive and the like, and a polyvinyl alcohol-based adhesive is suitable.

The surface of the dye-based polarizing plate of the present invention may be further provided with a transparent protective layer. The protective layer includes, for example, a hard coat layer comprising an acrylic-based resin or a polysiloxane-based resin, a protective layer comprising a urethane-based resin, and the like. In addition, in order for more improvement of the single plate light transmittance ratio, it is preferred to provide an AR layer (antireflection layer) on this protective layer. The AR layer can be formed, for example, by vapor deposition or sputtering treatment of a substance such as silicon dioxide, titanium oxide and the like. Further, the AR layer can be formed by thin-coating a fluorine-based substance.

In this regard, the dye-based polarizing plate of the present invention can be also used as an elliptically polarizing plate to which a retardation plate is attached.

The thus-constituted dye-based polarizing plate of the present invention has characteristics of no color-leaking in the orthogonal position in the wavelength region of the visible light region, having excellent polarization performance, and further, causing no discoloration and no reduction in polarization performance even in the state of high temperature and high humidity, and less light-leaking in the orthogonal position in the visible light region.

In addition, the dye-based polarizing plate of the present invention preferably has a single plate average light transmittance ratio (in wavelength region of 380 to 700 nm, or in a certain wavelength region in the color polarizing plate) of 38% or more, preferably 39% or more, more preferably 40% or more and further preferably 41% or more, and an average light transmittance in the orthogonal position of 0.4% or less, preferably 0.3% or less, more preferably 0.2% or less and further preferably 0.1% or less.

In the case where a polarizing plate having a neutral color hue such as neutral gray is made from the dye-based polarizing plate of the present invention, it can be obtained by adsorbing a plurality (for example, 2 to 4 kinds) of other dichroic dyes having the absorption maximum in a different wavelength region into a raw film for a polarizing film, together with the azo compound represented by the formula (1), by a common method so that the resulting polarizing film exhibits a neutral color, followed by orientating the film to obtain a polarizing film having a neutral color hue, which is then formed to be a polarizing plate as above.

Further, in the case of making a color polarizing plate, a color polarizing plate having an intended hue can be obtained by appropriately adsorbing, into a raw film for a polarizing film, the azo compound of the formula (1) of the present invention alone, or according to necessity, in combination with another dichroic organic dye according to an intended color, for example, blue, green, red or the like so as to have an intended hue, followed by orientation to give a color polarizing film, which is then formed to a polarizing plate by a common method.

A preferable polarizing plate containing the azo compound of the formula (1) of the present invention has a high polarization ratio of 99.9% or more and also a high contrast value of 100 or more, preferably 250 or more, more preferably 290 or more and further preferably 350 or more and a particularly preferable one has a high contrast value of 400 or more, so it can be suitably used for various liquid crystal displays according to the purpose. Furthermore, the polarizing plate of the present invention has excellent durability, so it can be suitably used for liquid crystal displays used under severe conditions (liquid crystal displays, liquid crystal projectors and the like which are used in the open air).

The color polarizing plate for a liquid crystal projector in the present invention contains the azo compound represented by the above formula (1) or a salt thereof as a dichroic coloring matter, and also according to necessity, together with the above other organic dye. The polarizing film to be used in the color polarizing plate for a liquid crystal projector of the present invention is also manufactured by the method described in the section of manufacturing method of the above dye-based polarizing film of the present invention. The color polarizing plate of the present invention obtained by attaching a protective film to the obtained polarizing film to give a polarizing plate, and according to necessity, by providing a protective or AR layer, a support and the like can be used as a color polarizing plate for a liquid crystal projector.

The color polarizing plate for a liquid crystal projector is preferably a color polarizing plate having a single plate average light transmittance ratio of 39% or more and an average light transmittance of 0.4% or less in the orthogonal position, in a required wavelength region corresponding to each color of said polarizing plate (A. the peak wavelength in the case of using an extra-high pressure mercury lamp: 420 to 500 nm for blue channel, 500 to 580 nm for green channel and 600 to 680 nm for red channel; and B. the peak wavelength in the case of using a 3 primary color LED lamp: 430 to 450 nm for blue channel, 520 to 535 nm for green channel and 620 to 635 nm for red channel). More preferable is a color polarizing plate having a single plate average light transmittance ratio of 41% or more and an average light transmittance of 0.3% or less and more preferably 0.2% or less in the orthogonal position, in a required wavelength region corresponding to each color of said polarizing plate. Further preferable is a color polarizing plate having a single plate average light transmittance ratio of 42% or more and an average light transmittance of 0.1% or less in the orthogonal position, in a required wavelength region corresponding to each color of said polarizing plate. The color polarizing plate for a liquid crystal projector containing the azo compound or a salt thereof of the present invention as a dichroic molecule is excellent in brightness and polarization performance.

In this regard, the term "single plate average light transmittance ratio" is a light ray transmittance average value in a certain wavelength region when a natural light enters one polarizing plate without providing a support such as an AR layer, a transparent glass plate and the like (hereinafter, when "polarizing plate" is referred for simplicity, it is used in the same meaning). The term "average light transmittance in the orthogonal position" is a light ray transmittance average value in a certain wavelength region when a natural light enters two polarizing plates with the orientation direction being arranged in the orthogonal position.

The liquid crystal display of the present invention may be one having a structure in which a light exiting from a light source such as an extra-high pressure mercury lamp (UHP lamp), a metal halide lamp or a white LED goes through a liquid crystal to display an image on a screen for displaying, where the polarizing film or plate of the present invention is arranged on either or both of the light source side (light-incident side) or the opposite side (light-exit side) from the light source in relation to the liquid crystal on the way of light in the above-described liquid crystal display so that a light exiting from the light source passes through the placed polarizing film or plate of the present invention.

The color polarizing plate for a liquid crystal projector of the present invention is preferably a polarizing plate with an AR layer where the polarizing plate comprising the polarizing film and the protective film of the present invention is provided with the above AR layer, and more preferably a polarizing plate with an AR layer and a support which is obtained by attaching a polarizing plate with an AR layer to a support such as a transparent glass plate.

The color polarizing plate for a liquid crystal projector of the present invention is usually used as a polarizing plate with a support. The support is preferably has a planar part to attach a polarizing plate, and in addition, it is preferably a transparent substrate for optical application. Specific examples of the transparent substrate include a glass plate, a lens, a prism (for example, triangular prism, cubic prism) and the like. A lens to which the polarizing plate is attached can be utilized as a condenser lens with a polarizing plate in a liquid crystal projector. In addition, a prism to which the polarizing plate is attached can be utilized as a polarization beam splitter with a polarizing plate or a dichroic prism with a polarizing plate in a liquid crystal projector. Further, the polarizing plate of the present invention may be attached to a liquid crystal cell.

The main types of the transparent substrate are the inorganic substrate and the organic substrate. Specific examples of the inorganic substrate include a soda glass, a borosilicate glass, a quartz substrate, a sapphire substrate, a spinel substrate and the like. Specific examples of the organic substrate include an organic substrate comprising acryl, polycarbonate and the like. The transparent substrate used for the polarizing plate with a support of the present invention is preferably an inorganic substrate. The transparent substrate may have desired thickness and size. Furthermore, the polarizing plate with a support (transparent substrate) of the present invention is preferably provided with an AR layer on either or both of its glass surface or its polarizing plate surface in order for more improvement of its single plate light transmittance ratio.

In order to manufacture the color polarizing plate with a support for a liquid crystal projector, for example, a transparent adhesive (sticking agent) is coated on a support planar part, and then the dye-based polarizing plate of the present invention may be attached to this coated surface. Or, a transparent adhesive (sticking agent) is coated on a polarizing plate, and then a support may be attached to this coated surface. As the adhesive (sticking agent) used here, a known adhesive and sticking agent can be used, and for example, an acrylic acid ester-based resin is preferable. In this regard, when the polarizing plate of the present invention accompanied with a retardation plate is used as an elliptically polarizing plate, a support is usually attached to the retardation plate side of the elliptically polarizing plate, but a support may be also attached to the polarizing plate side of the elliptically polarizing plate.

In a color liquid crystal projector using the dye-based polarizing plate of the present invention, the dye-based polarizing plate of the present invention is arranged on either or both of the incidence side or the exit side of a liquid crystal cell. Said polarizing plate may or may not be contacted with the liquid crystal cell, but is preferably not contacted from the viewpoint of durability. When the polarizing plate is contacted with the liquid crystal cell on the exit side, the dye-based polarizing plate of the present invention with a liquid crystal cell as a support can be used. When the polarizing plate is not contacted with the liquid crystal cell, it is preferred to use the dye-based polarizing plate of the present invention using a support other than a liquid crystal cell. In addition, from the viewpoint of durability, it is preferred to arrange the dye-based polarizing plate of the present invention on both the incident side and the exit side of the liquid crystal cell. Further it is preferred to arrange the polarizing plate surface of the dye-based polarizing plate with a support of the present invention on the opposite side of the light source and to arrange the support surface on the light source side. In this regard, the incident side of the liquid crystal cell refers to the light source side and the opposite side refers to the exit side.

The color liquid crystal projector using the dye-based polarizing plate of the present invention is preferably one with an ultraviolet-cut filter being arranged between a light source and a polarizing plate with a support on the above-described incident side. In addition, the liquid crystal cell to be used is preferably one which is, for example, an active matrix type and formed by enclosing a liquid crystal between a transparent substrate with an electrode and a TFT being formed and a transparent substrate with a counter electrode being formed.

A light emitted from a light source such as an extra-high pressure mercury lamp (UHP lamp), a metal halide lamp or a white LED is passed through an ultraviolet-cut filter and separated into three primary colors, which are then passed through a color polarizing plate with a support for each channel of blue, green and red, subsequently united and magnified by a projector lens to be projected on a screen. Otherwise, also known is the method in which a light emitted from each color LED of blue, green and red is passed through a color polarizing plate with a support for each channel of blue, green and red, and then united and magnified by a projector lens to project on a screen.

The thus-configured color polarizing plate for a liquid crystal projector has characteristics of being excellent in polarization performance, and further, causing no discoloration and no reduction in polarization performance even in the state of high temperature and high humidity.

EXAMPLE

Hereinafter, the present invention will be more specifically explained with reference to Examples but these are illustrative and do not limit the present invention. "%" and "part(s)" described below are based on mass unless otherwise particularly noted.

Example 1

To 500 parts of water, 38.3 parts of 7-aminonaphthalene-1,3,6-trisulfonic acid were added, and the mixture was cooled. Thereto, at 10° C. or less, 31.3 parts of 35% hydrochloric acid and then 6.9 parts of sodium nitrite were added, followed by stirring at 5 to 10° C. for 1 hour for diazotization. Thereto, 10.7 parts of 3-methylaniline dissolved in dilute hydrochloric acid water were added, and sodium carbonate was added to give pH 3 while stirring at 10 to 30° C. The mixture was further stirred to complete the coupling reaction, and the reaction liquid was filtered to obtain 40.1 parts of a monoazoamino compound represented by the following formula (67).

Formula (67)

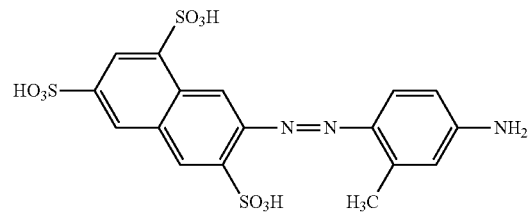

The obtained manoazoamino compound was added to 400 parts of water, and the mixture was dissolved with sodium hydroxide. Thereto, at 10 to 30° C., 25.0 parts of 35% hydrochloric acid and then 5.5 parts of sodium nitrite were added, followed by stirring at 20 to 30° C. for 1 hour for diazotization. Thereto, 8.6 parts of 3-methylaniline dissolved in dilute hydrochloric acid water were added, and sodium carbonate were added to give pH 3 while stirring at 20 to 30° C. The mixture was further stirred to complete the coupling reaction, and the reaction liquid was filtered to obtain 39.7 parts of a disazoamino compound represented by the following formula (68).

Formula (68)

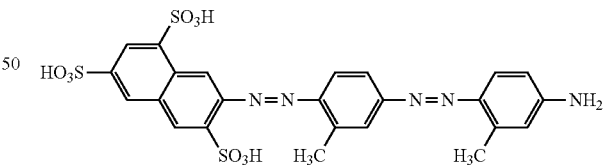

The obtained disazoamino compound was added to 250 parts of water, and the mixture was dissolved with sodium hydroxide. Thereto, at 20 to 30° C., 20.0 parts of 35% hydrochloric acid and then 4.4 parts of sodium nitrite were added, followed by stirring at 20 to 30° C. for 1 hour for diazotization. Thereto, 7.7 parts of 2,5-dimethylaniline dissolved in dilute hydrochloric acid water were added, and sodium carbonate was added to give pH 3.5 while stirring at 20 to 30° C. The mixture was stirred to complete the coupling reaction, and the reaction liquid was filtered to obtain 38.5 parts of a trisazoamino compound represented by the following formula (69).

Formula (69)

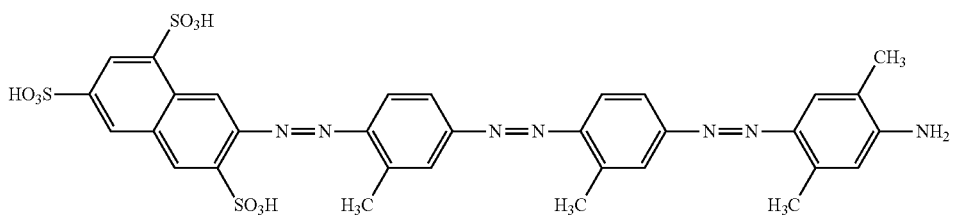

The obtained trisazoamino compound was added to 200 parts of water, and the mixture was dissolved with sodium hydroxide. Thereto, at 20 to 30° C., 16.0 parts of 35% hydrochloric acid and then 3.5 parts of sodium nitrite were added, followed by stirring at 20 to 30° C. for 1 hour for diazotization. Meanwhile, 16.1 parts of 6-phenylamino-1-naphthol-3-sulfonic acid were added to 50 parts of water, and the mixture was dissolved as weak alkaline with sodium carbonate. Into this liquid, a diazotized compound of the former-obtained trisazoamino compound was poured while maintaining at pH 8-10, followed by stirring to complete the coupling reaction. The reaction liquid was salted out with sodium chloride and filtered to obtain 27.6 parts of a tetrakisazo compound represented by the above formula (18). The maximum absorption wavelength of this compound in a 20% aqueous pyridine solution was 576 nm.

Example 2

In the same manner as in Example 1 except that 17.7 parts of 6-(4'-methoxyphenylamino)-1-naphthol-3-sulfonic acid were used as a quaternary coupler instead of 16.1 parts of 6-phenylamino-1-naphthol-3-sulfonic acid, 28.4 parts of a tetrakisazo compound represented by the above formula (17) were obtained. The maximum absorption wavelength of this compound in a 20% aqueous pyridine solution was 579 nm.

Example 3

In the same manner as in Example 1 except that 18.3 parts of 6-(4'-aminobenzoylamino)-1-naphthol-3-sulfonic acid were used as a quaternary coupler instead of 16.1 parts of 6-phenylamino-1-naphthol-3-sulfonic acid, 28.7 parts of a tetrakisazo compound represented by the above formula (23). The maximum absorption wavelength of this compound in a 20% aqueous pyridine solution was 562 nm.

Example 4

In the same manner as in Example 1 except that 28.2 parts of a naphthol represented by the following formula (70) were used as a quaternary coupler instead of 16.1 parts of 6-phenylamino-1-naphthol-3-sulfonic acid, 33.6 parts of a tetrakisazo compound represented by the above formula (26). The maximum absorption wavelength of this compound in a 20% aqueous pyridine solution was 574 nm.

Formula (70)

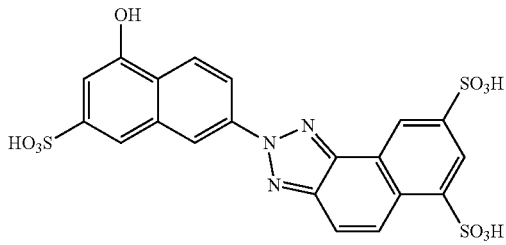

Example 5

In the same manner as in Example 1 except that 17.6 parts of 6-(4'-hydroxyphenylazo)-3-sulfo-1-naphthol were used as a quaternary coupler instead of 16.1 parts of 6-phenylamino-1-naphthol-3-sulfonic acid, 28.3 parts of a tetrakisazo compound represented by the above formula (27) were obtained. The maximum absorption wavelength of this compound in a 20% aqueous pyridine solution was 598 nm.

Example 6

In the same manner as in Example 1 except that 6.9 parts of 3-methylaniline were used as a tertiary coupler instead of 7.7 parts of 2,5-dimethylaniline, 28.0 parts of a tetrakisazo compound represented by the above formula (19) were obtained. The maximum absorption wavelength of this compound in a 20% aqueous pyridine solution was 565 nm.

Example 7

To 500 parts of water, 38.3 parts of 7-aminonaphthalene-1,3,6-trisulfonic acid were added, and the mixture was cooled. Thereto, at 10° C. or less, 31.3 parts of 35% hydrochloric acid and then 6.9 parts of sodium nitrite were added, followed by stirring at 5 to 10° C. for 1 hour for diazotization. Thereto, 12.1 parts of 2,5-dimethylaniline dissolved in dilute hydrochloric acid water were added, and sodium carbonate was added to give pH 3 while stirring at 10 to 30° C. The mixture was further stirred to complete the coupling reaction, and the reaction liquid was filtered to obtain 41.2 parts of a monoazoamino compound represented by the following formula (71).

Formula (71)

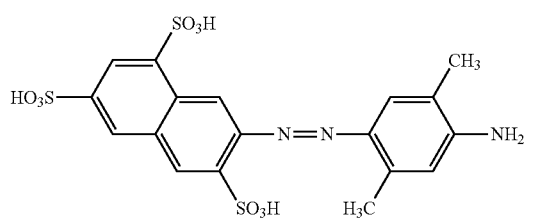

The obtained monoazoamino compound was added to 400 parts of water, and the mixture was dissolved with sodium hydroxide. Thereto, at 10 to 30° C., 25.0 parts of 35% hydrochloric acid and then 5.5 parts of sodium nitrite were added, followed by stirring at 20 to 30° C. for 1 hour for diazotization. Thereto, 9.7 parts of 2,5-dimethylaniline dissolved in dilute hydrochloric acid water were added, and sodium carbonate were added to give pH 3 while stirring at 20 to 30° C. The mixture was further stirred to complete the coupling reaction, and the reaction liquid was filtered to obtain 41.5 parts of a disazoamino compound represented by the following formula (72).

Formula (72)

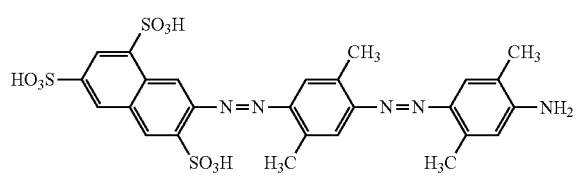

The obtained disazoamino compound was added to 250 parts of water, and the mixture was dissolved with sodium hydroxide. Thereto, at 20 to 30° C., 20.0 parts of 35% hydrochloric acid and then 4.4 parts of sodium nitrite were added, followed by stirring at 20 to 30° C. for 1 hour for diazotization. Thereto, 7.7 parts of 2,5-dimethylaniline dissolved in dilute hydrochloric acid water were added, and sodium carbonate was added to give pH 3.5 while stirring at 20 to 30° C. The mixture was further stirred to complete the coupling reaction, and the reaction liquid was filtered to obtain 39.9 parts of a trisazoamino compound represented by the following formula (73).

Formula (73)

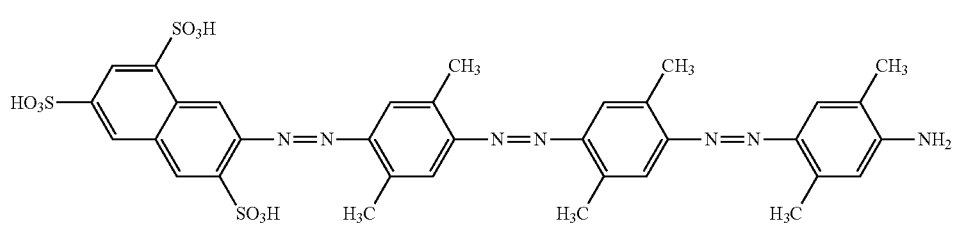

The obtained trisazoamino compound was added to 200 parts of water, and the mixture was dissolved with sodium hydroxide. Thereto, at 20 to 30° C., 16.0 parts of 35% hydrochloric acid and then 3.5 parts of sodium nitrite were added, followed by stirring at 20 to 30° C. for 1 hour for diazotization. Meanwhile, 17.7 parts of 6-(4'-methoxyphenylamino)-1-naphthol-3-sulfonic acid were added to 50 parts of water, and the mixture was dissolved as weak alkaline with sodium carbonate. Into this liquid, a diazotized compound of the former-obtained trisazoamino compound was poured while maintaining at pH 8-10, followed by stirring to complete the coupling reaction. The reaction liquid was salted out with sodium chloride and filtered to obtain 29.1 parts of a tetrakisazo compound represented by the above formula (8). The maximum absorption wavelength of this compound in a 20% aqueous pyridine solution was 575 nm.

Example 8

In the same manner as in Example 1 except that 16.1 parts of 6-phenylamino-1-naphthol-3-sulfonic acid were used as a quaternary coupler instead of 17.7 parts of 6-(4'-methoxyphenylamino)-1-naphthol-3-sulfonic acid, 28.3 parts of a tetrakisazo compound represented by the above formula (11) were obtained. The maximum absorption wavelength of this compound in a 20% aqueous pyridine solution was 575 nm.

Example 9

In the same manner as in Example 1 except that 18.3 parts of 6-(4'-aminobenzoylamino)-1-naphthol-3-sulfonic acid were used as a quaternary coupler instead of 17.7 parts of 6-(4'-methoxyphenylamino)-1-naphthol-3-sulfonic acid, 29.4 parts of a tetrakisazo compound represented by the above formula (12) were obtained. The maximum absorption wavelength of this compound in a 20% aqueous pyridine solution was 563 nm.

Example 10

To 500 parts of water, 36.1 parts of 6-amino-4-(3-sulfopropoxy)naphthalene-2-sulfonic acid were added, and the mixture was cooled. Thereto, at 10° C. or less, 31.3 parts of 35% hydrochloric acid and then 6.9 parts of sodium nitrite were added, followed by stirring at 5 to 10° C. for 1 hour for diazotization. Thereto, 12.1 parts of 2,5-dimethylaniline dissolved in dilute hydrochloric acid water were added, and sodium carbonate was added to give pH 3 while stirring at 10 to 30° C. The mixture was further stirred to complete the coupling reaction, and the reaction liquid was filtered to obtain 39.5 parts of a monoazoamino compound represented by the following formula (74).

Formula (74)

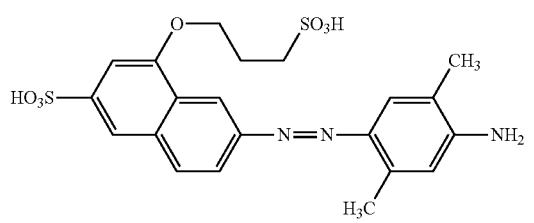

The obtained monoazoamino compound was added to 400 parts of water, and the mixture was dissolved with sodium hydroxide. Thereto, at 10 to 30° C., 25.0 parts of 35% hydrochloric acid and then 5.5 parts of sodium nitrite were added, followed by stirring at 20 to 30° C. for 1 hour for diazotization. Thereto, 19.6 parts of 3-(2-amino-4-methylphenoxy)propane-1-sulfonic acid dissolved in dilute hydrochloric acid water were added, and sodium carbonate was added to give pH 3 while stirring at 20 to 30° C. The mixture was further stirred to complete the coupling reaction, and the reaction liquid was filtered to obtain 48.0 parts of a disazoamino compound represented by the following formula (75).

The obtained trisazoamino compound was added to 200 parts of water, and the mixture was dissolved with sodium hydroxide. Thereto, at 20 to 30° C., 16.0 parts of 35% hydrochloric acid and then 3.5 parts of sodium nitrite were added, followed by stirring at 20 to 30° C. for 1 hour for diazotization. Meanwhile, 16.1 parts of 6-phenylamino-1-naphthol-3-sulfonic acid were added to 50 parts of water, and the mixture was dissolved as weak alkaline with sodium carbonate. Into this liquid, a diazotized compound of the former-obtained trisazoamino compound was poured while maintaining at pH 8-10, followed by stirring to complete the coupling reaction. The reaction liquid was salted out with sodium chloride and filtered to obtain 30.9 parts of a tetrakisazo compound represented by the above formula (9). The maximum absorption wavelength of this compound in a 20% aqueous pyridine solution was 586 nm.

Example 11

In the same manner as in Example 10 except that 36.1 parts of 7-amino-4-(3-sulfopropoxy)naphthalene-2-sulfonic acid were used as a starting material instead of 36.1 parts of 6-amino-4-(3-sulfopropoxy)naphthalene-2-sulfonic acid, 30.9 parts of a tetrakisazo compound represented by the Formula (75)

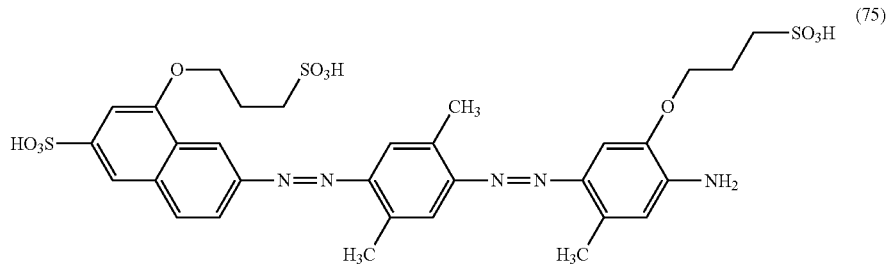

The obtained disazoamino compound was added to 250 parts of water, and the mixture was dissolved with sodium hydroxide. Thereto, at 20 to 30° C., 20.0 parts of 35% hydrochloric acid and then 4.4 parts of sodium nitrite were added, followed by stirring at 20 to 30° C. for 1 hour for diazotization. Thereto, 7.7 parts of 2,5-dimethylaniline dissolved in dilute hydrochloric acid water were added, and sodium carbonate was added to give pH 3.5 while stirring at 20 to 30° C. The mixture was further stirred to complete the coupling reaction, and the reaction liquid was filtered to obtain 45.2 parts of a trisazoamino compound represented by the following formula (76).

above formula (10) were obtained. The maximum absorption wavelength of this compound in a 20% aqueous pyridine solution was 587 nm.

Example 12

In the same manner as in Example 10 except that 18.3 parts of 6-(4'-aminobenzoylamino)-1-naphthol-3-sulfonic acid were used as a quaternary coupler instead of 16.1 parts of 6-phenylamino-1-naphthol-3-sulfonic acid, 32.0 parts of a tetrakisazo compound represented by the above formula (13)

Formula (76)

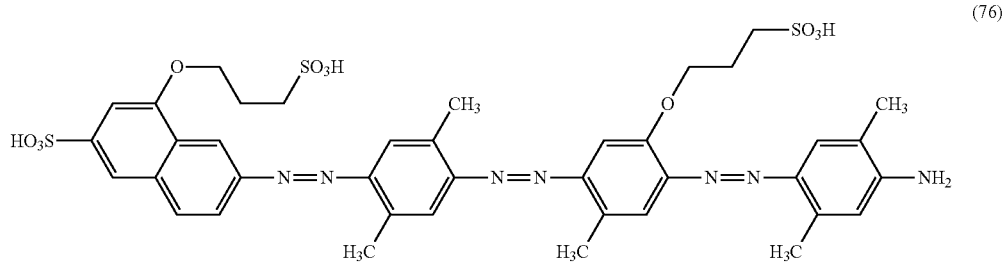

were obtained. The maximum absorption wavelength of this compound in a 20% aqueous pyridine solution was 575 nm.

Example 13

In the same manner as in Example 10 except that 24.5 parts of 3-(2-amino-4-methylphenoxy)propane-1-sulfonic acid were used as a primary coupler instead of 12.1 parts of 2,5-dimethylaniline and 9.7 parts of 2,5-dimethylaniline were used as a secondary coupler instead of 19.6 parts of 3-(2-amino-4-methylphenoxy)propane-1-sulfonic acid, 30.9 parts of a tetrakisazo compound represented by the above formula (14) were obtained. The maximum absorption wavelength of this compound in a 20% aqueous pyridine solution was 576 nm.

Example 14

In the same manner as in Example 10 except that 36.1 parts of 7-amino-4-(3-sulfopropoxy)naphthalene-2-sulfonic acid were used as a starting material instead of 36.1 parts of 6-amino-4-(3-sulfopropoxy)naphthalene-2-sulfonic acid, 24.5 parts of 3-(2-amino-4-methylphenoxy)propane-1-sulfonic acid were used as a primary coupler instead of 12.1 parts of 2,5-dimethylaniline and 9.7 parts of 2,5-dimethylaniline were used as a secondary coupler instead of 19.6 parts of 3-(2-amino-4-methylphenoxy)propane-1-sulfonic acid, 30.9 parts of a tetrakisazo compound represented by the above formula (15) were obtained. The maximum absorption wavelength of this compound in a 20% aqueous pyridine solution was 579 nm.

Example 15

In the same manner as in Example 10 except that 30.3 parts of 7-aminonaphthalene-1,3-disulfonic acid were used as a starting material instead of 36.1 parts of 6-amino-4-(3-sulfopropoxy)naphthalene-2-sulfonic acid and 17.7 parts of 6-(4'-methoxyphenylamino)-1-naphthol-3-sulfonic acid were used as a quaternary coupler instead of 16.1 parts of 6-phenylamino-1-naphthol-3-sulfonic acid, 32.0 parts of a tetrakisazo compound represented by the above formula (16) were obtained. The maximum absorption wavelength of this compound in a 20% aqueous pyridine solution was 588 nm.

Example 16

To 500 parts of water, 38.3 parts of 7-aminonaphthalene-1,3,6-trisulfonic acid were added, and the mixture was cooled. Thereto, at 10° C. or less, 31.3 parts of 35% hydrochloric acid and then 6.9 parts of sodium nitrite were added, followed by stirring at 5 to 10° C. for 1 hour for diazotization. Thereto, 13.7 parts of 2-methoxy-5-methylaniline dissolved in dilute hydrochloric acid water were added, and sodium carbonate was added to give pH 3 while stirring at 10 to 30° C. The mixture was further stirred to complete the coupling reaction, and the reaction liquid was filtered to obtain 42.5 parts of a monoazoamino compound represented by the following formula (77).

Formula (77)

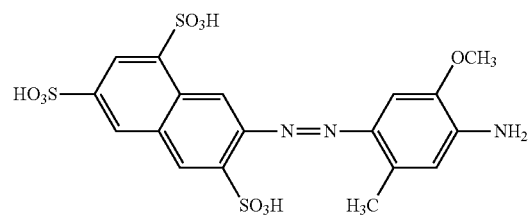

(77)

The obtained monoazoamino compound was added to 400 parts of water, and the mixture was dissolved with sodium hydroxide. Thereto, at 10 to 30° C., 25.0 parts of 35% hydrochloric acid and then 5.5 parts of sodium nitrite were added, followed by stirring at 20 to 30° C. for 1 hour for diazotization. Thereto, 9.7 parts of 2,5-dimethylaniline dissolved in dilute hydrochloric acid water were added, and sodium carbonate was added to give pH 3 while stirring at 20 to 30° C. The mixture was further stirred to complete the coupling reaction, and the reaction liquid was filtered to obtain 42.5 parts of a disazoamino compound represented by the following formula (78).

Formula (78)

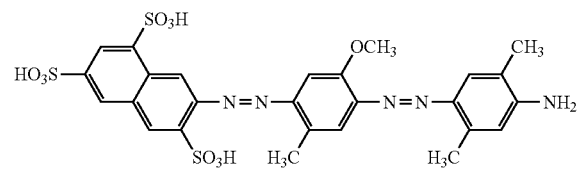

(78)

The obtained disazoamino compound was added to 250 parts of water, and the mixture was dissolved with sodium hydroxide. Thereto, at 20 to 30° C., 20.0 parts of 35% hydrochloric acid and then 4.4 parts of sodium nitrite were added, followed by stirring at 20 to 30° C. for 1 hour for diazotization. Thereto, 7.7 parts of 2,5-dimethylaniline dissolved in dilute hydrochloric acid water were added, and sodium carbonate was added to give pH 3.5 while stirring at 20 to 30° C. The mixture was further stirred to complete the coupling reaction, and the reaction liquid was filtered to obtain 40.8 parts of a trisazoamino compound represented by the following formula (79).

Formula (79)

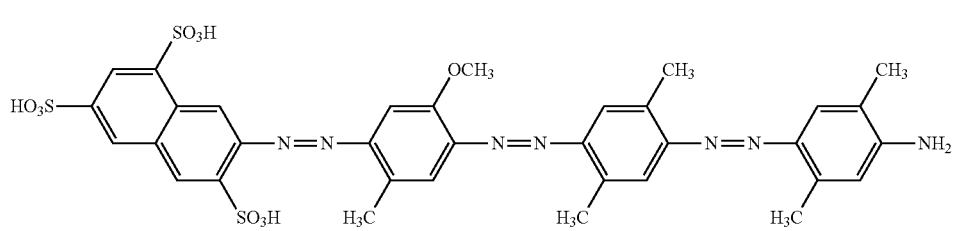

(79)

The obtained trisazoamino compound was added to 200 parts of water, and the mixture was dissolved with sodium hydroxide. Thereto, at 20 to 30° C., 16.0 parts of 35% hydrochloric acid and then 3.5 parts of sodium nitrite were added, followed by stirring at 20 to 30° C. for 1 hour for diazotization. Meanwhile, 17.7 parts of 6-(4'-methoxyphenylamino)-1-naphthol-3-sulfonic acid were added to 50 parts of water, and the mixture was dissolved as weak alkaline with sodium carbonate. Into this liquid, a diazotized compound of the former-obtained trisazoamino compound was poured while maintaining at pH 8-10, followed by stirring to complete the coupling reaction. The reaction liquid was salted out with sodium chloride and filtered to obtain 29.5 parts of a tetrakisazo compound represented by the above formula (20). The maximum absorption wavelength of this compound in a 20% aqueous pyridine solution was 582 nm.

Example 17

In the same manner as in Example 16 except that 8.6 parts of 3-methylaniline were used as a secondary coupler instead of 9.7 parts of 2,5-dimethylaniline, 29.1 parts of a tetrakisazo compound represented by the above formula (21) were obtained. The maximum absorption wavelength of this compound in a 20% aqueous pyridine solution was 582 nm.

Example 18

In the same manner as in Example 16 except that 16.1 parts of 6-phenylamino-1-naphthol-3-sulfonic acid were used as a quaternary coupler instead of 17.7 parts of 6-(4'-methoxyphenylamino)-1-naphthol-3-sulfonic acid, 28.7 parts of a tetrakisazo compound represented by the above formula (22) were obtained. The maximum absorption wavelength of this compound in a 20% aqueous pyridine solution was 579 nm.

Example 19

In the same manner as in Example 16 except that 11.0 parts of 2-methoxy-5-methylaniline were used as a secondary coupler instead of 9.7 parts of 2,5-dimethylaniline, 29.9 parts of a tetrakisazo compound represented by the above formula (24) were obtained. The maximum absorption wavelength of this compound in a 20% aqueous pyridine solution was 592 nm.

Example 20

In the same manner as in Example 16 except that 11.0 parts of 2-methoxy-5-methylaniline were used as a secondary coupler instead of 9.7 parts of 2,5-dimethylaniline and 16.1 parts of 6-phenylamino-1-naphthol-3-sulfonic acid were used as a quaternary coupler instead of 17.7 parts of 6-(4'-methoxyphenylamino)-1-naphthol-3-sulfonic acid, 29.1 parts of a tetrakisazo compound represented by the above formula (25) were obtained. The maximum absorption wavelength of this compound in a 20% aqueous pyridine solution was 590 nm.

Example 21

In an aqueous solution of 45° C. containing the compound of the above formula (18) obtained in Example 1 at a concentration of 0.03% and a sodium sulfate at a concentration of 0.1%, a polyvinyl alcohol film having a thickness of 75 μm was immersed for 4 minutes. This film was stretched 5 times in a 3% aqueous boric acid solution at 50° C., washed with water and dried while maintaining the tension state, to obtain a polarizing film of the present invention.

The obtained polarizing film has a maximum absorption wavelength of 581 nm and a polarization ratio of 99.9%, thus having a high polarization ratio.

The test method will be mentioned below.

The maximum absorption wavelength and polarization ratio of the polarizing film is calculated after the parallel transmittance ratio at the time of polarized light incidence and the orthogonal transmittance ratio were measured using a spectrophotometer (U-4100 manufactured by Hitachi, Ltd.). Here, the parallel transmittance ratio (Ky) is a transmittance ratio when the absorption axis of a polarizing film and the absorption axis of a polarizing film are parallel to each other, and the orthogonal transmittance ratio (Kz) refers to a transmittance ratio when the absorption axis of a polarizing film and the absorption axis of a polarizing film are orthogonal to each other.

The parallel transmittance ratio and orthogonal transmittance ratio of each wavelength were measured at 1 nm intervals from 380 to 780 nm. Using each measured value, the polarization ratio of each wavelength was calculated according to the following formula (1), and the wavelength where the polarization ratio was highest at 380 to 780 nm was defined as the maximum absorption wavelength (nm) of the polarizing film. The obtained maximum absorption wavelength of the polarizing film and the polarization ratio at that time are shown in Table 1.

$$\text{Polarization ratio (\%)} = [(Ky-Kz)/(Ky+Kz)] \times 100 \qquad (i)$$

Examples 22 to 40

In the same manner as in Example 21 except that each azo compound represented by the formulas (8) to (17) and the formulas (19) to (27) obtained in Examples 2 to 20 was used instead of the compound of the above formula (18), a polarizing film of the present invention was obtained.

The azo compounds or a salt thereof used in Examples, the maximum absorption wavelengths of the obtained polarizing films and the polarization ratios at that time are shown in Table 1.

As is in Table 1, any of the polarizing films using these compounds had a high polarization ratio.

TABLE 1

| Example | Azo compound or a salt thereof | Maximum absorption wavelength (nm) | Polarization ratio (%) |
|---|---|---|---|
| 21 | Compound of the formula (18) | 581 | 99.9 |
| 22 | Compound of the formula (8) | 593 | 99.9 |
| 23 | Compound of the formula (9) | 584 | 99.9 |
| 24 | Compound of the formula (10) | 592 | 99.9 |
| 25 | Compound of the formula (11) | 582 | 99.9 |
| 26 | Compound of the formula (12) | 566 | 99.9 |
| 27 | Compound of the formula (13) | 571 | 99.9 |
| 28 | Compound of the formula (14) | 581 | 99.9 |
| 29 | Compound of the formula (15) | 587 | 99.9 |
| 30 | Compound of the formula (16) | 593 | 99.9 |
| 31 | Compound of the formula (17) | 590 | 99.9 |
| 32 | Compound of the formula (19) | 578 | 99.9 |
| 33 | Compound of the formula (20) | 594 | 99.9 |
| 34 | Compound of the formula (21) | 591 | 99.9 |
| 35 | Compound of the formula (22) | 581 | 99.9 |
| 36 | Compound of the formula (23) | 560 | 99.9 |
| 37 | Compound of the formula (24) | 604 | 99.9 |
| 38 | Compound of the formula (25) | 594 | 99.9 |
| 39 | Compound of the formula (26) | 564 | 99.9 |
| 40 | Compound of the formula (27) | 578 | 99.9 |

Example 41

One index representing image quality is a contrast showing luminance difference between the white display and the black display. The maximum absorption wavelengths of the polarizing films obtained in Examples 21 to 23, 25, 28, 30 to 32, 34 to 37, and 39 and the contrasts at that time are shown in Table 2. Here, the contrast shows the ratio of a parallel transmittance ratio to an orthogonal transmittance ratio (contrast=parallel transmittance ratio (Ky)/orthogonal transmittance ratio (Kz)), and it is meant that higher this value is, more excellent the polarization performance of the polarizing plate is.

In this regard, for the contrast (polarization performance), a sample was made so that the polarizing films had an equal parallel transmittance ratio in the maximum absorption wavelength, and comparison was conducted.

The maximum absorption wavelength of each-obtained polarizing film and the contrast in the maximum absorption wavelength were calculated from the parallel transmittance ratio and orthogonal transmittance ratio measured using a spectrophotometer (U-4100 manufactured by Hitachi, Ltd.). The obtained evaluation results of the polarizing films are shown in Table 2. As shown in Table 2, any of the polarizing films made using a compound of the present invention had a high contrast.

Comparative Example 1

According to the method described in the example 7 of Patent Literature 5, a compound represented by the following formula (80) was synthesized.

Formula (80)

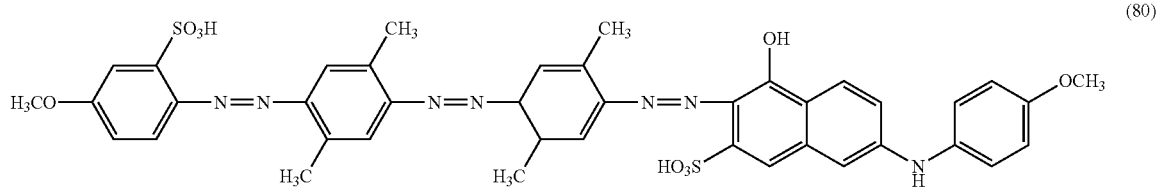

Using the compound represented by the above-described formula (80) instead of the compound represented by the formula (18), a polarizing film was made in accordance with the method described in Example 21 so as to have a parallel transmittance ratio, in the maximum absorption wavelength, equal to that of each polarizing film obtained Example 41, and the maximum absorption wavelength and contrast of the polarizing film was calculated in the same manner as in Example 41. As shown in Table 2, any of the polarizing films of the present invention showed a high contrast and had excellent polarization performance, relative to Comparative Example 1.

Comparative Example 2

According to the method described in the example 2 of Patent Literature 6, a compound represented by the following formula (81) was synthesized.

Formula (81)

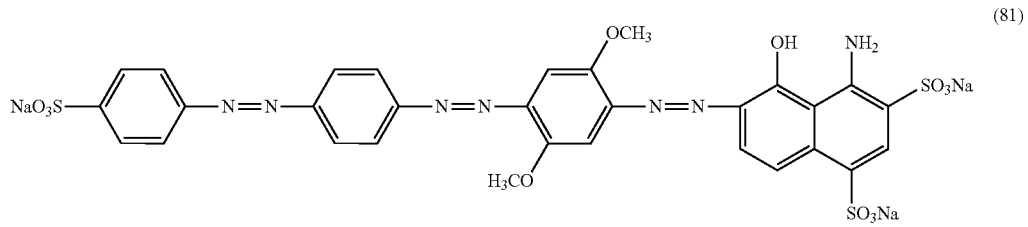

Using the compound represented by the above-described formula (81) instead of the compound represented by the formula (18), a polarizing film was made in accordance with the method described in Example 21 so as to have a parallel transmittance ratio, in the maximum absorption wavelength, equal to that of each polarizing film obtained in Example 41, and the maximum absorption wavelength and contrast of the polarizing film was calculated in the same manner as in Example 41. As shown in Table 2, any of the polarizing films of the present invention showed a high contrast and had excellent polarization performance, relative to Comparative Example 2.

Comparative Example 3

According to the method described in Patent Literature 7, p. 21, paragraph 0077, a compound represented by the following formula (82) was synthesized.

Formula (82)

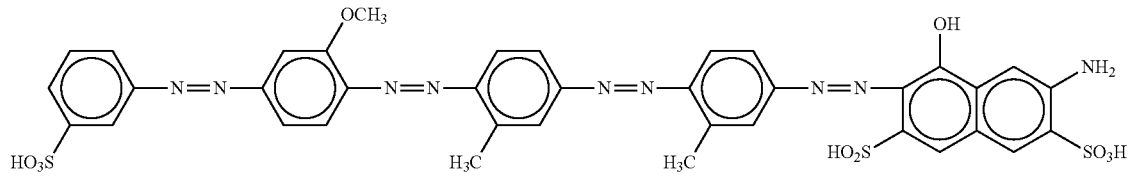

(82)

Using the compound represented by the above-described formula (82) instead of the compound represented by the formula (18), a polarizing film was made in accordance with the method described in Example 21 so as to have a parallel transmittance ratio, in the maximum absorption wavelength, equal to that of each polarizing film obtained in Example 41, and the maximum absorption wavelength and contrast of the polarizing film was calculated in the same manner as in Example 41. As shown in Table 2, any of the polarizing films of the present invention showed a high contrast and had excellent polarization performance, relative to Comparative Example 3.

TABLE 2

| Azo compound or a salt thereof | Maximum absorption wavelength (nm) | Contrast |
|---|---|---|
| Compound of the formula (18) | 581 | 426 |
| Compound of the formula (8) | 593 | 331 |
| Compound of the formula (9) | 584 | 376 |
| Compound of the formula (11) | 582 | 406 |
| Compound of the formula (14) | 581 | 258 |
| Compound of the formula (16) | 593 | 297 |
| Compound of the formula (17) | 590 | 296 |
| Compound of the formula (19) | 578 | 426 |
| Compound of the formula (21) | 591 | 268 |
| Compound of the formula (22) | 581 | 361 |
| Compound of the formula (23) | 560 | 428 |
| Compound of the formula (24) | 604 | 320 |
| Compound of the formula (26) | 564 | 343 |
| Compound of the formula (80) (Comparative Example 1) | 586 | 64 |
| Compound of the formula (81) (Comparative Example 2) | 664 | 79 |
| Compound of the formula (82) (Comparative Example 3) | 590 | 67 |

Example 42

A cellulose triacetate film (TAC Film; manufactured by FUJIFILM Corporation; trade name: TD-80U) was laminated via an adhesive of an aqueous polyvinyl alcohol solution on both surfaces of the polarizing film obtained in Example 31 to make a polarizing plate of the present invention. A glass plate was attached to one surface of the obtained polarizing plate using a sticking agent to make a polarizing plate with a support of the present invention. The obtained polarizing plate with a support was light-irradiated with an accelerated xenon arc tester (SX-75; manufactured by Suga Test Instruments Co., Ltd.) for 190 hours and the change in the polarization ratio before and after irradiation was measured. The change in the polarization ratio was calculated as {(polarization ratio before irradiation)−(polarization ratio after irradiation)}/(polarization ratio before irradiation), resulting in 0.37%, and thus the polarizing plate of the present invention showed excellent durability.

Examples 43 to 45

Using each polarizing film obtained Examples 22, 26 and 32, a polarizing plate with a support of the present invention was made and change in the polarization ratio before and after light-irradiation was measured, in the same manner as in Example 42. As the result, as shown in Table 3, any of the polarizing plates of the present invention showed excellent durability.

TABLE 3

| Example | Polarizing film | Azo compound or a salt thereof | Change of polarization ratio (%) |
|---|---|---|---|
| 42 | Example 31 | Compound of the formula (17) | 0.37 |
| 43 | Example 22 | Compound of the formula (8) | 0.36 |
| 44 | Example 26 | Compound of the formula (12) | 0.35 |
| 45 | Example 32 | Compound of the formula (19) | 0.50 |
| Comparative Example 4 | Comparative Example 1 | Compound of the formula (80) | 1.80 |
| Comparative Example 5 | Comparative Example 2 | Compound of the formula (81) | 1.38 |

Comparative Examples 4 to 5

Using each polarizing film obtained in Comparative Examples 1 to 2, a polarizing plate with a support of the present invention was made and change in the polarization ratio before and after light-irradiation was measured, in the same manner as in Example 42. As the result, as shown in Table 3, it is shown that the polarizing plate of the present invention had excellent durability compared with the polarizing plates of Comparative Examples 4 to 5.

In the same manner as in Example 21 except for using, as a dye bath, an aqueous solution of 45° C. containing a compound (18) of the present invention obtained in Example 1 at a concentration of 0.2%, C.I. Direct orange 39 at a concentration of 0.07%, C.I. Direct red 81 at a concentration of 0.02%, and a sodium sulfate at a concentration of 0.1%, a polarizing film of the present invention was made. The obtained polarizing film had a maximum absorption wavelength of 555 nm, a single panel average transmittance of 42% in 530 to 570 nm, and an average light transmittance of 0.02% in the orthogonal position, thus having a high degree of polarization.

A cellulose triacetate film (TAC Film; manufactured by FUJIFILM Corporation; trade name: TD-80U) was attached to one surface of this polarizing film and a film with an about 10 μm ultraviolet curable hard coat layer formed on one side of said TAC Film was attached to the other surface, to obtain a polarizing plate of the present invention. For attachment of the TAC Film, an adhesive of an aqueous polyvinyl alcohol solution was used. An acrylic acid ester-based sticking agent was given to the surface of the obtained polarizing plate with no hard coat layer being formed, and also an AR (antireflection) multi-coating was applied to the outside of the hard coat layer by vacuum vapor deposition. The obtained polarizing plate with an AR layer was cut into a size of 30 mm×40 mm and attached to a same size and transparent glass plate with an AR layer on one side, to obtain a polarizing plate with an AR layer and support of the present invention (for a liquid crystal projector green channel). The polarizing plate with an AR layer and a support of the present invention had a high polarization ratio and showed durability for a long period of time even in the state of high temperature and high humidity. Also it had excellent fastness to light exposure for a long period of time.

INDUSTRIAL APPLICABILITY

The polarizing film and the polarizing plate containing the azo compound or a salt thereof of the present invention have high polarization performance comparable to a polarizing film and a polarizing plate using iodine as a dichroic coloring matter and are also excellent in durability. Therefore, by containing the azo compound or a salt thereof of the present invention, and according to necessity, another dichroic dye, a color polarizing film or a neutral color polarizing film suitable for various liquid crystal display bodies, color liquid crystal projectors, in-vehicle application requiring high polarization performance and durability, and display application of industrial instruments used for various environments can be provided.

The invention claimed is:

1. A dye-based polarizing film containing in a raw film for a polarizing film, an azo compound and/or a salt thereof, which is represented by the following formula (7):

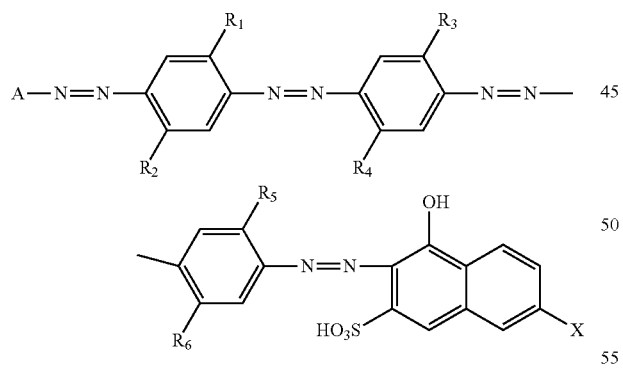

(7)

in the formula (7), A represents a naphthyl group having a substituent; $R_1$ to $R_6$ each independently represent a hydrogen atom, an alkyl group having a carbon atom number of 1 to 5, an alkoxy group having a carbon atom number of 1 to 5, a sulfo group or an alkoxy group having a sulfo group and a carbon atom number of 1 to 5, X represents a phenylamino group, a phenylazo group, or a naphthotriazole group, wherein A is a naphthyl group represented by the following formula (6):

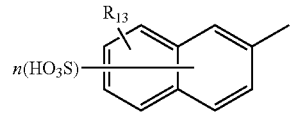

(6)

in the formula (6), $R_{13}$ represents a hydrogen atom, a sulfo group, a hydroxy group, or an alkoxy group having a sulfo group and a carbon atom number of 1 to 5, and n represents 1 to 3;

wherein the phenylamino group is represented by the following formula (2):

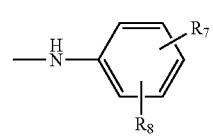

(2)

in the formula (2), $R_7$ and $R_8$ each independently represent a hydrogen atom, a methyl group, a methoxy group, a sulfo group, an amino group or a substituted amino group;

wherein the phenylazo group is represented by the following formula (5):

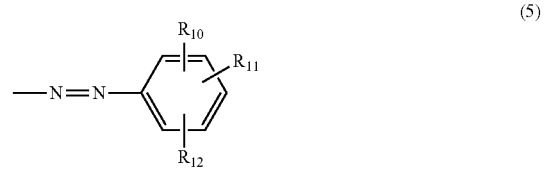

(5)

in the formula (5), $R_{10}$ to $R_{12}$ each independently represent a hydrogen atom, a hydroxy group, an alkyl group having a carbon atom number of 1 to 5, an alkoxy group having a carbon atom number of 1 to 5, an amino group or a substituted amino group; and wherein the naphthotriazole group is represented by the following formula (4):

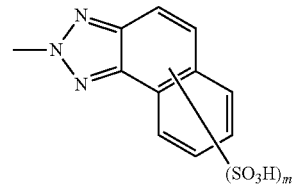

(4)

in the formula (4), m represents 1 or 2.

2. The dye-based polarizing film containing the azo compound and/or a salt thereof according to claim 1, wherein $R_1$ to $R_6$ are each independently a hydrogen atom, a methyl group, a methoxy group, or an alkoxy group having a sulfo group and a carbon atom number of 1 to 5.

3. The dye-based polarizing film containing the azo compound and/or a salt thereof according to claim 1, wherein A is a naphthyl group substituted with 2 or 3 sulfo groups (m represents 2), or a naphthyl group substituted with a 3-sulfopropoxy group and a sulfo group ($R_{13}$ is a 3-sulfopropoxy group and n represents 1); $R_1$, $R_3$ and $R_5$ are each independently a hydrogen atom, a methyl group, a methoxy group or a 3-sulfopropoxy group; $R_2$, $R_4$ and $R_6$ are methyl groups; and X is any one group selected from the group consisting of an unsubstituted phenylamino group ($R_7$ and $R_8$ are hydrogen atoms), a phenylamino group substituted with a methoxy group (one of $R_7$ and $R_8$ is a methoxy group and the other is a hydrogen atom), or a naphthotriazole substituted with 2 sulfo groups (m=2).

4. The dye-based polarizing film containing at least one kind of the azo compound and/or a salt thereof according to claim 3 and one or more kinds of other dichroic organic dyes.

5. The dye-based polarizing film containing two or more kinds of the azo compound and/or a salt thereof according to claim 3 and one or more kinds of other dichroic organic dyes.

6. The dye-based polarizing film according to claim 3, wherein the raw film for a polarizing film is a film comprising a polyvinyl alcohol resin, a vinyl alcohol copolymer resin or a modified form of a polyvinyl alcohol resin.

7. The dye-based polarizing film according to claim 6, wherein the raw film for a polarizing film is a polyvinyl alcohol resin film.

8. A dye-based polarizing plate with a transparent protective film attached to at least one surface comprising the dye-based polarizing film according to claim 3.

9. A liquid crystal display comprising the dye-based polarizing plate according to claim 8.

10. The dye-based polarizing film containing at least one kind of the azo compound and/or a salt thereof according to claim 1 and at least one or more kinds of other dichroic organic dyes.

11. The dye-based polarizing film containing at least two or more kinds of the azo compound and/or a salt thereof according to claim 1 and one or more kinds of other dichroic organic dyes.

12. The dye-based polarizing film containing at least one kind of the azo compound and/or a salt thereof according to claim 1 is a color dye-based polarizing film.

13. The dye-based polarizing film according to claim 1, wherein the raw film for a polarizing film is a film comprising a polyvinyl alcohol resin, a vinyl alcohol copolymer resin or a modified form of a polyvinyl alcohol resin.

14. The dye-based polarizing film according to claim 13, wherein the raw film for a polarizing film is a polyvinyl alcohol resin film.

15. A dye-based polarizing plate with a transparent protective film attached to at least one surface comprising the dye-based polarizing film according to claim 1.

16. A liquid crystal display comprising the dye-based polarizing plate according to claim 15.

17. A liquid crystal projector comprising the dye-based polarizing film according to claim 1 or a dye-based polarizing plate with a transparent protective film attached to at least one surface of said dye-based polarizing film.

* * * * *